(12) United States Patent
Stelzig et al.

(10) Patent No.: US 10,040,969 B2
(45) Date of Patent: Aug. 7, 2018

(54) COMPOSITE FILLER PARTICLES AND PROCESS FOR THE PREPARATION THEREOF

(71) Applicant: DENTSPLY International Inc., York, PA (US)

(72) Inventors: Simon Stelzig, Constance (DE); Jörg Kempter, Constance (DE); Stephanie Noerpel, Constance (DE); Joachim E. Klee, Radolfzell (DE); Andreas Facher, Gundetswil (CH); Uwe Walz, Constance (DE); Christoph Weber, Constance (DE)

(73) Assignee: DENTSPLY SIRONA Inc., York, PA (US)

( * ) Notice: Subject to any disclaimer, the term of this patent is extended or adjusted under 35 U.S.C. 154(b) by 0 days.

(21) Appl. No.: 14/872,557

(22) Filed: Oct. 1, 2015

(65) Prior Publication Data
US 2016/0024334 A1    Jan. 28, 2016

Related U.S. Application Data

(62) Division of application No. 13/714,803, filed on Dec. 14, 2012, now Pat. No. 9,193,849.

(30) Foreign Application Priority Data

Dec. 15, 2011 (EP) .................................. 11009866

(51) Int. Cl.
| | |
|---|---|
| C08J 3/12 | (2006.01) |
| C08J 3/24 | (2006.01) |
| C08K 3/40 | (2006.01) |
| C09D 143/04 | (2006.01) |
| A61K 6/00 | (2006.01) |
| A61K 6/083 | (2006.01) |
| C03C 17/00 | (2006.01) |
| C09C 3/00 | (2006.01) |
| B05D 7/24 | (2006.01) |
| C08K 5/5419 | (2006.01) |
| C09C 1/40 | (2006.01) |
| C09C 3/04 | (2006.01) |
| C09C 3/08 | (2006.01) |
| C09C 3/12 | (2006.01) |
| A61K 6/02 | (2006.01) |
| C03C 14/00 | (2006.01) |
| C03C 17/30 | (2006.01) |
| B01J 2/16 | (2006.01) |

(52) U.S. Cl.
CPC .......... *C09D 143/04* (2013.01); *A61K 6/0008* (2013.01); *A61K 6/0076* (2013.01); *A61K 6/0085* (2013.01); *A61K 6/0091* (2013.01); *A61K 6/024* (2013.01); *A61K 6/025* (2013.01); *A61K 6/0215* (2013.01); *A61K 6/083* (2013.01); *B01J 2/16* (2013.01); *B05D 7/24* (2013.01); *C03C 14/008* (2013.01); *C03C 17/00* (2013.01); *C03C 17/30* (2013.01); *C08K 3/40* (2013.01); *C08K 5/5419* (2013.01); *C09C 1/40* (2013.01); *C09C 3/00* (2013.01); *C09C 3/006* (2013.01); *C09C 3/045* (2013.01); *C09C 3/08* (2013.01); *C09C 3/12* (2013.01); *C01P 2004/61* (2013.01); *C03C 2214/12* (2013.01)

(58) Field of Classification Search
USPC ......................... 523/342, 116, 214; 427/213
See application file for complete search history.

(56) References Cited

U.S. PATENT DOCUMENTS

| | | | | | |
|---|---|---|---|---|---|
| 4,781,940 | A | * | 11/1988 | Denton, Jr. ............... | C08F 2/44 427/2.14 |
| 5,055,497 | A | * | 10/1991 | Okada .................. | A61K 6/0017 523/115 |
| 6,121,344 | A | * | 9/2000 | Angeletakis ......... | A61K 6/0073 523/115 |
| 2008/0196627 | A1 | * | 8/2008 | Sproson .................... | C03C 8/14 106/287.34 |
| 2008/0317794 | A1 | * | 12/2008 | Gellermann ........... | A61K 8/025 424/401 |

* cited by examiner

*Primary Examiner* — Tae H Yoon
(74) *Attorney, Agent, or Firm* — Sushma Chauhan; Douglas Hura; David A. Zdurne

(57) ABSTRACT

A process for the preparation of composite filler particles, comprising: (a) coating a particulate filler having a median particle size (D50) of from 1 to 1200 nm; (b) agglomerating the coated particulate filler, for providing a granulation of the coated particulate filler wherein the granulation contains the coated particulate filler particles whereby the at least one coating layer may be crosslinked by crosslinking groups obtained by reacting the reactive groups and optionally a further crosslinking agent.

16 Claims, 8 Drawing Sheets

COMPOSITE FILLER PARTICLES AND PROCESS FOR THE PREPARATION THEREOF

RELATED APPLICATIONS

This patent application is a divisional patent application of U.S. patent application Ser. No. 13/714,803, now U.S. Pat. No. 9,193,849, which claims the benefit of and priority to EP Application Ser No. 11009866.2, filed on Dec. 15, 2011, which is herein incorporated by reference for all purposes.

FIELD OF THE INVENTION

The present invention relates to a process for the preparation of composite filler particles. Moreover, the present invention also relates to composite filler particles obtainable by the process according to the present invention. Furthermore, the present invention relates to the use of the composite filler particles in a dental composition such as a dental restorative material. The composite filler particles of the invention have a high content of inorganic filler for providing improved mechanical properties and reduced polymerization shrinkage without impairing workability due to an increase of viscosity. Moreover, the composite filler particles provide excellent aesthetic properties due to improved surface properties of a dental restoration prepared by a procedure including a polishing step. The composite filler particles have an essentially spherical shape.

BACKGROUND OF THE INVENTION

Dental restorative materials for use in the preparation of crowns, veneers, direct fillings, inlays, onlays and splints are known. Dental restorative materials such as dental composites contain a curable resin and particulate filler. However, resin shrinkage upon polymerization in the curing process tends to cause gap formation between the restorative composite and the tooth. As a consequence micro leakage, secondary caries and decreased longevity of the repair represents a problem with prior dental restorative materials. In order to alleviate the shrinking problem and to reinforce dental restorative materials, particulate fillers are commonly used, whereby a high filler load is preferred.

EP 1 396 254 discloses a particulate prepolymerized filler prepared by mixing an inorganic filler with an organic polymerizable resin and curing the mixture. Specifically, fumed silica and a barium aluminoborosilicate glass are mixed with polymerizable resin to prepare a paste and the paste is then heat polymerized and the resultant polymerized mass is ground to the desired particle size, for example, using a ceramic ball mill. The prepolymerized filler disclosed by EP 1 396 254 has an inorganic load of about 55 percent by volume and is used to enable higher filler loading of a dental restorative composition while maintaining acceptable handling properties of the paste.

However, the prepolymerized filler of EP 1 396 254 is problematic regarding the mechanical and chemical resistance compared to the properties of the particulate glass which is used for preparing the prepolymerized filler.

Moreover, since the prepolymerized filler must be ground and classified before incorporation into a dental restorative composition, the prepolymerized filler of EP 1 396 254 requires additional time and energy consuming process steps.

WO 0130304 discloses filler particles for use in a dental restorative composition, which comprise clusters of nano-sized metal oxide particles and further non-agglomerated nano-sized particles. The clusters are made using a process that includes heat treatment of a spray dried sol of metal oxide particles. The filler particles are silanated and incorporated into a dental restorative composition in an amount of about 78 parts by weight. WO 0130304 suggests that the clusters provide strength, while the nano-sized particles provide aesthetic quality, polishability, and wear resistance. However, the filler is problematic in that spray-drying and calcining metal oxide sol particles provide a product which requires milling in a ball mill for 160 hours in order to achieve an average cluster size of 1 μm.

The particulate filler materials of the prior art are not satisfactory when used in a dental restorative material having high filler loading for reduced shrinkage while being mechanically strong. A high filler loading results in a viscosity problem, which may usually be addressed by using large filler particles. Large filler particles generally provide a lower viscosity as compared to smaller filler particles. However, a cured product of a composition containing large filler particles is unsatisfactory regarding the polishability since a smooth surface may hardly be obtained due to large filler particles being removed from the surface of the cured product leaving cavities impairing the aesthetic properties.

U.S. Pat. No. 6,020,395 discloses a homogeneous microfilled dental composite material comprised of a mixture of polymerizable monomers and an inorganic filler, wherein said filler is comprised of silane treated fused silica aggregates having a size ranging from submicron to about 160 μm. The aggregates are comprised of agglomerates of fumed silica having an average agglomerate size in the range of approximately 0.5 to 50 μm, and the agglomerates are comprised of primary particles of fumed silica having an average particle size in the range of approximately 1 to 100 nm. The primary particles are interconnected by siloxane bridges formed by burning an organosilane coating on the fumed silica. According to Example 1, raw OX-50 was coated with 20% by weight A-174 organosilane in a V-blender using an aqueous solution spray, dried in a forced air oven at 100° C. for 24 hours, and hammermilled to a 10 μm average particle size. The silane-coated OX-50 was oxidized at 1050° C. for 4 hours, resulting in bridged silica particles (fused silica). The fused silica was then surface treated with 7% by weight A-174 organosilane in a V-blender using an aqueous solution spray. The silane-treated fused silica was dried at 110° C. for 3 hours and at 55° C. for 16 hours, then sieved through 95 mesh. The resulting filler consisted of agglomerates of Si—O bridged 0.04 μm fumed silica with aggregates of 10 μm mean size and a range of from submicron to 160 μm.

U.S. Pat. No. 4,781,940 discloses a process for the production of a filler for use in a microfilled dental composite formulation, which process comprises the steps of: (a) coating colloidal silica with a polymerizable monomer by mixing said silica with an organic solvent solution of said monomer and an effective amount of a polymerization catalyst, and then evaporating said solvent; (b) individualizing the coated silica by screening to product particles having a maximum size of about 90 microns; (c) polymerizing said monomer; and (d) individualizing the coated silica particles comprising the product of step (c) by screening. The filler of U.S. Pat. No. 4,781,940 consists of particles having an irregular shape thereby causing undesireably high viscosity increases when used in a dental composition.

SUMMARY OF THE INVENTION

It is a problem of the present invention to provide composite filler particles which affords high filler loading, high strength and excellent polishability after curing of a dental restorative material containing the particulate composite filler while maintaining appropriate viscosity for good workability of the dental restorative material, and lower shrinkage during polymerization, as well as process for the preparation of a particulate filler.

The present invention provides a process for the preparation of composite filler particles, comprising:
(a) coating a particulate filler having a median particle size (D50) of from 1 to 1200 nm with a coating composition containing a film-forming agent forming a coating layer on the surface of the particulate filler, said coating layer displaying reactive groups on the surface of the coating layer, said reactive groups being selected from addition polymerizable groups and step-growth polymerizable groups, thereby forming a coated particulate filler; subsequently or concurrently
(b) agglomerating the coated particulate filler, optionally in the presence of a further crosslinking agent and optionally in the presence of a further particulate filler not displaying reactive groups, for providing a granulation of the coated particulate filler wherein the granulation contains the coated particulate filler particles and the optional further particulate filler particles separated from and connected to each other by at least one coating layer, whereby the at least one coating layer may be crosslinked by crosslinking groups obtained by reacting the reactive groups and optionally a further crosslinking agent;
(c) optionally milling, classifying and/or sieving the granulation of the coated particulate filler; and
(d) optionally further crosslinking the granulation of the coated particulate filler; for providing composite filler particles having a median particle size (D50) of from 1 to 70 wherein reactive groups are transformed into crosslinking groups obtained by reacting reactive groups and optionally a further crosslinking agent, and wherein the particulate filler is the main component by volume of the composite filler particles.

According to the present invention, agglomeration may be carried out by spray agglomeration or growth agglomeration, whereby spray agglomeration is preferred.

According to the present invention, the reactive groups of the granulation of the coated particulate filler comprised in the composite particulate filler is partially crosslinked. Crosslinking may be due to crosslinking groups obtained by reacting the reactive groups and optionally a further crosslinking agent in the step of agglomerating the coated particulate filler, optionally in the presence of a further crosslinking agent and optionally in the presence of a further particulate filler not displaying reactive groups, for providing a granulation of the coated particulate filler. Alternatively or additionally, crosslinking may be due to crosslinking the granulation of the coated particulate filler after the agglomeration step (a), or after the optional step of milling, classifying and/or sieving the granulation of the coated particulate filler.

Moreover, the present invention also provides a particulate composite filler obtainable by the process according to the invention. The particulate composite filler of the present invention comprises generally spherical primary composite filler particles, in particular generally sherical primary composite particles oibtainable by spray agglomeration. Primary particles are particles which cannot be reduced in size by breaking up aggregated particles, for example, by using sonication.

The particulate composite filler of the present invention comprises residual reactive groups such as polymerizable double bonds due to the incomplete crosslinking of reactive groups. The residual reactive groups may react with further reactive groups of a curable matrix in which the particulate composite filler is dispersed. Specifically, residual polymerizable double bonds of the particulate composite filler of the present invention may react with a polymerizable matrix of a dental composition when the particulate composite filler is used in a dental composition.

Furthermore, the present invention provides a use of the particulate composite filler of the present invention in a dental composition.

The present invention is based on the recognition that it is possible to efficiently and effectively prepare a composite filler particles having a high inorganic filler load by coating primary particles of a particulate filler with a coating composition containing a specific reactive film-forming agent forming a coating layer on the surface of the particulate filler. Based on the coated particulate filler, a granulation may be provided wherein the granulation contains the coated particulate filler particles separated from each other by at least one coating layer. Crosslinking of the reactive groups of the specific reactive film-forming agent stabilizes the granulation by covalent bonding whereby composite filler particles of the present invention are obtained.

According to the process of the present invention, it is not necessary to use time and energy consuming milling steps while at the same time, the process of the present invention provides control over the particle size distribution so that a large amount of fines or coarse particles as side products are avoided.

The composite filler particles may be obtained with a large particle size for incorporation into a highly filled dental composition whereby the viscosity and the workability of the dental composition are excellent. A cured dental composition provides a material having a high filler loading, high strength and excellent polishability and shows low shrinkage during polymerization.

DETAILED DESCRIPTION OF THE PREFERRED EMBODIMENTS

Figure 1:
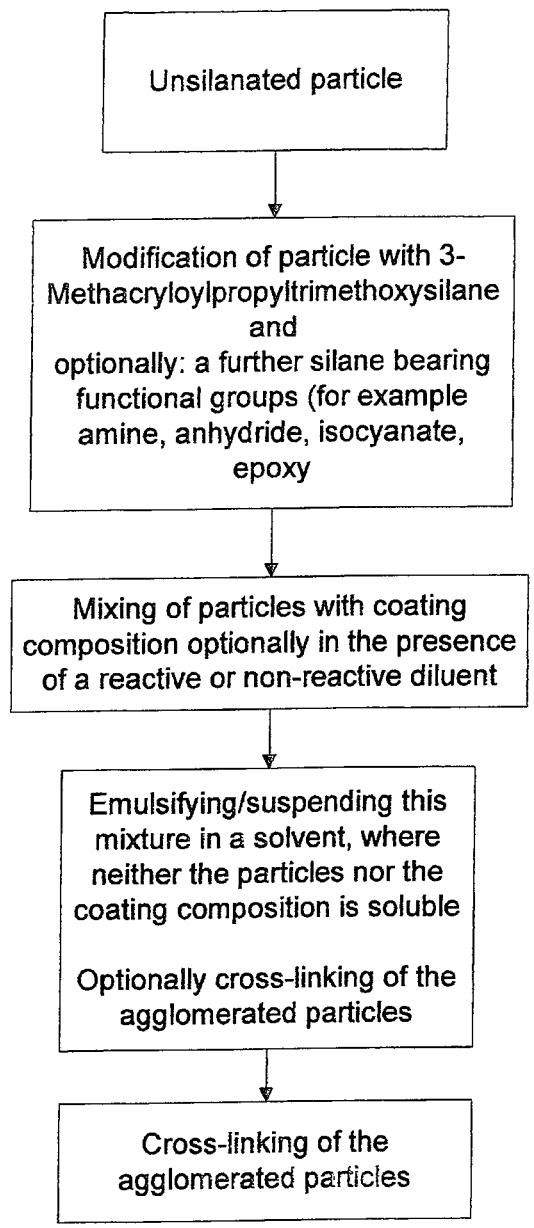
FIG. 1 is a flow chart illustrating a first generic embodiment of the process of the present invention based on a suspension/emulsion technique.

The present invention provides a composite filler particles. The composite filler particles are particularly useful for the preparation of a dental composition. A dental composition is preferably a dental restorative material. The dental restorative material may be selected from a dental composite, a dental cement or a resin reinforced dental cement. A dental composite may be a highly filled dental composite, a flowable composite, a compomer, a root canal sealer, or a pit and fissure sealant. A dental cement may be a glass ionomer cement or a luting cement.

The particulate filler is the main component by volume of the composite filler particles. Accordingly, more than 50 percent by volume, preferably more than 60 percent by volume, still more preferably more than 70 percent by volume of the composite filler particles are occupied by a particulate filler.

In order to provide a high volume of the particulate filler in the composite filler particles, the maximum thickness of the coating layer on the particulate filler is preferably less than the median particle diameter (D50) of the particulate filler. According to a preferred embodiment, the maximum thickness of the coating layer is less than 100 percent of the median particle diameter (D50) of the particulate filler, more preferably less than 50 percent of the median particle diameter. More preferably, the maximum thickness of the coating layer is less than 20 percent of the median particle diameter (D50) of the particulate filler.

Preferably, the composite filler particles have a porosity of at most 20 percent, preferably at most 15 percent, a still more preferred at most 10 percent, as measured by the mercury method in accordance with DIN 66 133.

The composite filler particles of the present invention have a median particle size (D50) of from 1 to 70 μm, preferably, 2 to 50 μm. The median particle size (D50) is measured after any aggregates of the composite filler particles have been broken up and dispersed, for example, by sonication for about 10 minutes in a suitable dispersion medium. In case agglomeration is carried out by using spray agglomeration, the median median particle size (D50) is preferably in the range of from 1 to 40 μm, more preferably, in the range of from 2 to 30 μm. In case agglomeration is carried out by using growth agglomeration, the median median particle size (D50) is preferably in the range of from 30 to 70 μm, more preferably, in the range of from 40 to 60 μm.

The particulate composite filler obtained by the process of the present invention comprises generally spherical primary composite filler particles. The primary particles need not be truly spherical, but should at least be rounded to the extent that a fluid-like movement of the particles is not substantially impeded. The spherical shape of the generally spherical primary particles is the result of the agglomeration of the coated particulate filler according to the present invention and does not require an additional milling step.

In the composite filler particles according to the present invention, reactive groups are transformed into crosslinking groups by reacting reactive groups and optionally a further crosslinking agent. Accordingly, the initial amount of reactive groups displayed by the coating layers of the coated particulate filler is reduced in the composite filler particles of the invention. The reaction products of the reactive groups and optionally the further crosslinking agent may be observed in the composite filler particles of the present invention.

A residual amount of reactive groups displayed by the composite filler particles may be beneficial for the incorporation and crosslinking of the composite filler particles in a dental composition. In case, the residual reactive groups are addition polymerizable groups, e.g. (meth)acryl groups, such residual reactive groups may take part in the curing reaction based on a radical polymerization of a polymerizable resin matrix of a dental composition in which the composite filler particles of the present invention are used. In case, the residual reactive groups are step-growth polymerizable groups, e.g. amino groups, carboxylic acid anhydride groups, or epoxide groups, such residual reactive groups may take part in the curing reaction of a dental composition based on a step-growth polymerization of a step-growth polymerizable resin matrix containing corresponding step-growth polymerigable groups.

The residual amount of reactive groups may be determined based on the degree of polymerization of monomers used for the preparation of the composite particulate filler. Preferably the degree of polymerization of the monomers is at least 50% and less than 100% and more preferably from 80% to 95% as determined by any of the methods disclosed in Example 8.

It is also within the concept of the present invention to treat the composite filler particles obtained by the process according to the present invention with a silanating agent or surface active agent in order to modify the surface properties of the composite filler particles and/or to introduce additional reactive groups or different reactive groups. Additional reactive groups may be reactive groups capable of undergoing the same type of polymerization selected from addition polymerization and step-growth polymerization as the reactive groups already displayed by the composite particulate filler. Different reactive groups may be reactive groups capable of undergoing the other type of polymerization selected from addition polymerization and step-growth polymerization as the reactive groups already displayed by the composite particulate filler.

Suitable silanating agents are any silanating agents which are conventionally used in the dental field, in particular those which are described herein for the preparation of a modified particulate filler, vide infra.

Suitable surface active agents may be selected from surfactants which preferable contain one or more reactive groups.

In the composite filler particles, the particulate filler is the main component by volume.

According to the present invention, the reactive groups of the granulation of the coated particulate filler comprised in the composite particulate filler are partially crosslinked. Preferably, crosslinking is due to crosslinking the granulation of the coated particulate filler after the agglomeration step (a), or after the optional step of milling, classifying and/or sieving the granulation of the coated particulate filler. However, some crosslinking during the agglomeration step (a) may be occur depending on the conditions used for the agglomeration and the presence of an initiator system.

The Step of Coating a Particulate Filler

The composite filler particles are prepared according to the present invention by a process comprising a step of coating a particulate filler with a coating composition.

The coating step may be carried out by dispersing the particulate filler in a suitable dispersing fluid. The dispersing fluid may be a liquid or gaseous dispersing fluid. If necessary, the particulate filler may be dispersed by using high shear forces. High shear forces may be applied by mechanical stirring, ultrasonication or atomization using a nozzle. It is preferred that the particulate filler is highly dispersed for increasing the surface of the particulate filler which is accessible for the film forming agent during the coating step.

In case the dispersing fluid is gaseous, as examples of the dispersing fluid any gas such as nitrogen, argon, or air may be mentioned as long as the gas does not interfere with the preparation of the composite filler particles according to the present invention. The gaseous dispersing fluids may used alone or as a mixture of two or more gases.

In case the dispersing fluid is a liquid, as examples of suitable liquids any conventional solvents may be mentioned as long as the liquid does not interfere with the preparation of the composite filler particles of the present invention, such as tetrahydrofurane, 1,4-dioxane, acetone, ethanol, propanol, pentane, hexane, heptane, cyclohexane, toluene, xylene, chloroform, methylene chloride, methyl ethyl ketone, methyl isobutyl ketone, diethyl ether, tert.-butylmethyl and ether. The liquid dispersing fluids may used alone or as a mixture of two or more liquids in amounts which are miscible with each other.

The dispersion may generally be carried out at a temperature of from $-20$ to $250°$ C. In case of a liquid dispersing agent, the dispersion may be carried out at a temperature to below the boiling point of the liquid solvent. Preferably, the dispersion step is carried out at a temperature in the range of from $10°$ C. to $150°$ C. The dispersion may be carried out for up to 10 hours, preferably from 10 seconds to 1 hour.

The Particulate Filler

The particulate filler has a median particle size (D50) of 1 to 1200 nm, preferably of from 10 to 1000 still more preferably of from 20 to 800 nm as measured using, for example, electron microscopy or by using a conventional laser diffraction particle sizing method as embodied by a MALVERN Mastersizer S or MALVERN Mastersizer 2000 apparatus.

According to a specific embodiment, the particulate filler has a median particle size (D50) of 100 to 800 nm.

The particulate filler is not particularly limited as long as the material of the particulate filler is acceptable for dental applications. Preferable particulate fillers for use in a dental composite may be selected from inorganic particulate filler including dental glasses, fused silica, quartz, crystalline silica, amorphous silica, soda glass beads, glass rods, ceramic oxides, particulate silicate glass, radiopaque glasses (barium and strontium glasses), and synthetic minerals. It is also possible to employ finely divided materials and powdered hydroxyl-apatite, although materials that react with silane coupling agents are preferred. Also available as a filler are colloidal or submicron oxides or mixed oxides. Suitable inorganic fillers are also $YF_3$, $La_2O_3$, $ZrO_2$, $BiPO_4$, $CaWO_4$, $BaWO_4$ $SrF_2$, $Bi_2O_3$.

Preferable particulate fillers for use in a dental cement or a resin reinforced dental cement are reactive. A reactive particulate filler is a powdered metal oxide or hydroxide, mineral silicate, or ion leachable glass or ceramic, that is capable of reacting with an acid in the presence of water. Examples of particulate reactive filler materials include materials commonly known in the art of glass-ionomer cements such as calcium or strontium-containing and aluminum-containing materials. Preferably, particulate reactive fillers contain leachable fluoride ions. Specific examples of particulate reactive fillers are selected from calcium alumino silicate glass, calcium alumino fluorosilicate glass, calcium aluminumfluoroborosilicate glass, strontium aluminosilicate glass, strontium aluminofluorosilicate glass, strontium aluminofluoroborosilicate glass. The glass may furthermore contain zirconium and/or barium. Suitable particulate reactive fillers further include metal oxides such as zinc oxide and magnesium oxide, and ion-leachable glasses, e.g., as described in U.S. Pat. No. 3,655,605, U.S. Pat. No. 3,814,717, U.S. Pat. No. 4,143,018, U.S. Pat. No. 4,209,434, U.S. Pat. No. 4,360,605 and U.S. Pat. No. 4,376,835.

A preferred particulate filler is a particulate glass filler selected from calcium alumino silicate glass, calcium alumino fluorosilicate glass, calcium aluminumfluoroborosilicate glass, strontium aluminosilicate glass, strontium aluminofluorosilicate glass, strontium aluminofluoroborosilicate glass, a strontium-aluminum-sodium-fluoride-phosphoroussilicate glass, and barium aluminum borosilicate glass, which has a median particle size (D50) of 100 to 800 nm.

The particulate filler may be a multimodal particulate filler representing a mixture of two or more particulate fractions having different average particle sizes. The particulate filler may also be a mixture of particles of different chemical composition. In particular, it is possible to use a mixture of a reactive particulate material and a non-reactive particulate material.

The particulate filler used in the coating step may also comprise final composite filler particles of the present invention. Specifically, composite filler particles having a small median particle size (D50) of 1 to 1200 nm may be separated from a composite filler of the present invention and recycled into the process of the present invention in order to provide composite filler particles having an increased median particle size (D50) of from 1 to 70 µm.

The surface of the particulate filler of the present invention may be modified prior to the coating step. Accordingly, the surface modifying agent contains a modifying compound capable of reacting with surface atoms of the particulate filler, thereby forming a covalent bond between the surface atoms of the particulate filler and the modifying compound. Additionally, the modifying compound may contain one or more polymerizable double bonds reactive in the crosslinking reaction after the particulate filler is agglomerated. The modifying agent may contain one or more modifying compounds. Preferably, the modifying compound provides a polymerizable ligand capable of crosslinking which may be a compound of one of the following formulae (I), (II) and (III), or a hydrolysis product thereof $$X_r R_{3-r} SiL \qquad (I)$$

$$X_r R_{2-r} SiL'L'' \qquad (II)$$

$$X_r SiL'L''L''' \qquad (III)$$

wherein
X represents a hydrolyzable group;
R represents an alkyl, cycloalky, cycloalkylalkyl, aralkyl or aryl group,
L, L', L", and L"'
  which may be the same or different represent independent from each other an organic group containing one or more polymerizable double bonds;
r is an integer of 1 to 3,
whereby the sum of X, R, L, L', L", and L"' is 4 for each of formula (I), (II), and (III).

Preferably, X is a halogen atom or $OR^1$, wherein $R^1$ is an alkyl, cycloalky, cycloalkylalkyl, aralkyl or aryl group. More preferably, R or $R^1$ are independently an alkyl group.

In order to impart crosslinking capability to the organofunctional silicon compound, L, L', L", and L'" contain one or more polymerizable double bonds capable of taking part in a crosslinking reaction. In a preferred embodiment, L, L', L", and L'" may be selected from the group of allyl, (meth)acrylic ester groups, and (meth)acrylic amide groups.

An alkyl group may be straight-chain or branched C1-16 alkyl group, typically a C1-8 alkyl group. Examples for a C1-6 alkyl group can include linear or branched alkyl groups having 1 to 6 carbon atoms, preferably 1 to 4 carbon atoms, for example, methyl, ethyl, n-propyl, isopropyl, n-butyl, isobutyl, sec-butyl, tert-butyl, n-pentyl, isopentyl and n-hexyl. A cycloalkyl group may be a C3-16 cycloalkyl group. Examples of the cycloalkyl group can include those having 3 to 14 carbon atoms, for example, cyclopropyl, cyclobutyl, cyclopentyl and cyclohexyl. A cycloalkylalkyl group can include those having 4 to 22 carbon atoms. Examples for a cycloalkylalkyl group can include a combination of a linear or branched alkyl group having 1 to 6 carbon atoms and a cycloalkyl group having 3 to 14 carbon atoms. Examples of the cycloalkylalkyl group can for example, include methylcyclopropyl, methylcyclobutyl, methylcyclopentyl, methylcyclohexyl, ethylcyclopropyl, ethylcyclobutyl, ethylcyclopentyl, ethylcyclohexyl, propylcyclopropyl, propylcyclobutyl, propylcyclopentyl, propylcyclohexyl. An aralkyl group may be a C7-26 aralkyl group, typically a combination of a linear or branched alkyl group having 1 to 6 carbon atoms and an aryl group having 6 to 10 carbon atoms. Specific examples of an aralkyl group are a benzyl group or a phenylethyl group. An aryl group can include aryl groups having 6 to 10 carbon atoms. Examples of the aryl group are phenyl and naphtyl.

The C1-6 alkyl group and the C3-14 cycloalkyl group may optionally be substituted by one or more members of the group selected from a C1-4 alkyl group, C1-4 alkoxy group, a phenyl group, and a hydroxy group. Examples for a C1-4 alkyl group can include linear or branched alkyl groups having 1 to 4 carbon atoms, for example, methyl, ethyl, n-propyl, isopropyl, n-butyl, isobutyl, sec-butyl, tert-butyl. Examples for an C1-4 alkoxy group can include linear or branched alkoxy groups having 1 to 4 carbon atoms, for example, methoxy, ethoxy, n-propoxy, isopropoxy, n-butoxy, isobutoxy, sec-butoxy, and tert-butoxy.

Aryl groups may contain 1 to 3 substituents. Examples of such substituents can include halogen atoms, C1-4 alkyl groups, C1-4 alkoxy groups, C1-4 alkylthio groups, C1-4 alkylsulfonyl groups, carboxyl group, C2-5 alkoxycarbonyl groups, and C1-4 alkylamino groups. Here, illustrative of the halogen atoms can be fluorine, chlorine, bromine and iodine. The C1-4 alkyl groups are, for example, methyl, ethyl, n-propyl, isopropyl and n butyl. Illustrative of the C1-4 alkoxy groups are, for example, methoxy, ethoxy and propoxy. Illustrative of the C1-4 alkylthio groups are, for example, methylthio, ethylthio and propylthio. Illustrative of the C1-4 alkylsulfonyl groups are, for example, methylsulfonyl, ethylsulfonyl and propylsulfonyl. Illustrative of the C2-5 alkoxycarbonyl groups can be those having alkoxy groups each of which contains 1 to 4 carbon atoms, for example, methoxycarbonyl, ethoxy carbonyl and propoxycarbonyl. Illustrative of the C1-8 alkylamino groups can be those having one or two alkyl groups each of which contains 1 to 4 carbon atoms, for example, methylamino, dimethylamino, ethyl amino and propylamino. The alkyl moieties in these substituents may be linear, branched or cyclic.

A preferred particulate filler is a particulate glass filler selected from calcium alumino silicate glass, calcium alumino fluorosilicate glass, calcium aluminumfluoroborosilicate glass, strontium aluminosilicate glass, strontium aluminofluorosilicate glass, strontium aluminofluoroborosilicate glass, and barium aluminum borosilicate glass, which has a median particle size (D50) of 200 to 800 nm, and which is surface-modified a modifying compound of one of the above formulae (I), (II) and (III), or a hydrolysis product thereof, as defined above.

The Coating Composition

The particulate filler is coated with a coating composition. The coating composition contains a film-forming agent forming a coating layer on the surface of the particulate filler said coating layer displaying reactive groups on the surface of the coating layer, said reactive groups being selected from addition polymerizable groups and step-growth polymerizable groups, thereby forming a coated particulate filler. The film-forming agent may form a covalent bond with functional groups on the surface of the particulate filler. For Example, the film-forming agent may silanate the surface of the particulate filler. Alternatively, the film forming agent may adhere to the surface of the particulate filler by non-covalent interaction such as by ionic forces or van der Waals forces. In case the film-forming agent forms a covalent bond, it is preferred that the film-forming agent carries a silyl group. In case the film forming agent adheres based on non-covalent forces, it is preferred that the particulate filler is modified by a modifying agent.

The coated particulate filler is reactive based on the reactive groups and forms crosslinking groups based on a reaction between reactive groups on particulate filler particles and optionally reactive groups of a crosslinking agent.

The reactive groups may be addition polymerizable groups or step-growth polymerizable groups. Addition polymerizable groups may be selected from ethylenically unsaturated groups such as (meth)acrylate groups, or vinyl groups. The step-growth polymerizable groups are selected from the group of amino groups, hydroxyl groups, isocyanate groups, and carboxylic acid anhydride groups.

Accordingly, the film-forming agents may comprise a polymerizable monomer which may be preferably selected from compounds characterized by one of the following formulas:

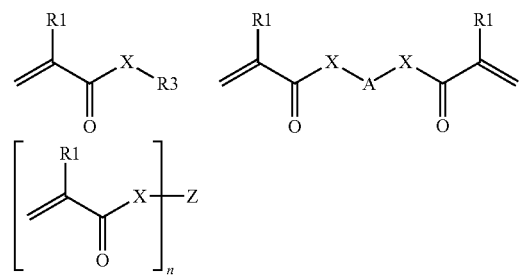

wherein X independently is O or NR2, wherein R1, R2, and R3 independently represent a hydrogen atom or a C1 to C8 alkyl group which may be substituted; A represents a divalent substituted or unsubstituted organic residue having from 1 to 40 carbon atoms which may be substituted, whereby said organic residue may contain from 1 to 6 oxygen and/or nitrogen atoms; Z represents a saturated at least trivalent substituted or unsubstituted C1 to C8 hydrocarbon group, a saturated at least trivalent substituted or unsubstituted cyclic C3 to C8 hydrocarbon group, and n is at least 3. The optionally substituted moieties R1, R2, R3, A, and Z may be substituted with from 1 to 6 acidic groups selected from carboxylic acid groups, phosphate ester groups, phosphonate groups, and sulfonic acid groups.

According to a first embodiment, X is O. According to a second embodiment, X is NR1 whereby the second embodiment provides a coating having increased hydrolysis stability.

The film-forming agents may also comprise polymerizable compounds which are selected from acrylates and methacrylates such as methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate (HEMA), hydroxypropyl acrylate, hydroxypropyl methacrylate, tetrahydrofurfuryl acrylate, tetrahydrofurfuryl methacrylate, glycidyl acrylate, glycidyl methacrylate, the diglycidyl methacrylate of bis-phenol A ("bis-GMA"), glycerol mono- and di-acrylate, glycerol mono- and di-methacrylate, ethyleneglycol diacrylate, ethyleneglycol dimethacrylate, polyethyleneglycol diacrylate (where the number of repeating ethylene oxide units vary from 2 to 30), polyethyleneglycol dimethacrylate (where the number of repeating ethylene oxide units vary from 2 to 30 especially triethylene glycol dimethacrylate ("TEGDMA"), neopentyl glycol diacrylate, neopentylglycol dimethacrylate, trimethylolpropane triacrylate, trimethylol propane trimethacrylate, mono-, di-, tri-, and tetra-acrylates and methacrylates of pentaerythritol and dipentaerythritol, 1,3-butanediol diacrylate, 1,3-butanediol dimethacrylate, 1,4-butanedioldiacrylate, 1,4-butanediol dimethacrylate, 1,6-hexane diol diacrylate, 1,6-hexanediol dimethacrylate, di-2-methacryloyloxethyl hexamethylene dicarbamate, di-2-methacryloyloxyethyl trimethylhexanethylene dicarbamate, di-2-methacryloyl oxyethyl dimethylbenzene dicarbamate, methylene-bis-2-methacryloxyethyl-4-cyclohexyl carbamate, di-2-methacryloxyethyl-dimethylcyclohexane dicarbamate, methylene-bis-2-methacryloxyethyl-4-cyclohexyl carbamate, di-1-methyl-2-methacryloxyethyl-trimethylhexamethylene dicarbamate, di-1-methyl-2-methacryloxyethyl-dimethyl benzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-metha-cryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl4-cyclohexyl carbamate, 2,2'-bis(4-methacryloxyphenyl)propane, 2,2'bis(4-acryloxyphenyl)propane, 2,2'-bis[4(2-hydroxy-3-methacryloxy-phenyl)]propane, 2,2'-bis[4(2-hydroxy-3-acryloxy-phenyl)propane, 2,2'-bis(4-methacryloxyethoxyphenyl)propane, 2,2'-bis(4-acryloxyethoxyphenyl)propane, 2,2'-bis(4-methacryloxypropoxyphenyl)propane, 2,2'-bis(4-acryloxypropoxyphenyl)propane, 2,2'-bis(4-methacryloxydiethoxyphenyl)propane, 2,2'-bis(4-acryloxydiethoxyphenyl)propane, 2,2'-bis[3(4-phenoxy)-2-hydroxypropane-1-methacrylate]propane, and 2,2'-bis[3(4-phenoxy)-2-hydroxypropane-1-acryalte]propane, may be mentioned. Other suitable examples of polymerizable components are isopropenyl oxazoline, vinyl azalactone, vinyl pyrrolidone, styrene, divinylbenzene, urethane acrylates or methacrylates, epoxy acrylates or methacrylates and polyol acrylates or methacrylates. Preferably, the polymerizable compound has a molecular weight of at most 10,000 Da, more preferably at most 8000 Da, and still mor preferably, 5000 Da.

Step-growth polymerizable groups may be selected from groups capable of undergoing condensation reactions for forming linkages such as urethane, ether, amine, amide or ester linkages. Alternatively, step-growth polymerizable groups may be selected from groups undergoing addition reactions for forming linkages such as amine linkages by e.g. a Michael addition.

A preferred class of film-forming agents forming a coating layer on the surface of the particulate filler are amino group containing silanes or siloxanes suitable for crosslinking with isocyanates, isocyanate/amine mixtures, isocyanate/diol mixtures, epoxides, epoxide/amine mixtures, anhydrides, carboxylic acids such as polyacrylic acid.

The amino group containing silanes or siloxanes may be selected from 3-aminopropyltriethoxysilane (APTES), 3-aminopropyltrimethoxysilane, m-aminophenyltrimethoxysilane, p-aminophenyltrimethoxysilane, 3-aminopropyltris (methoxyethoxyethoxy)silane, 3-(m-aminophenoxy)propyltrimethoxysilane, 3-Aminopropylmethyldiethoxysilane, 3-aminopropyldimethylethoxysilane, N-(2-aminoethyl)-3-aminopropyltrimetoxysilane, aminopropylmethyldimethoxysilane, aminopropyldimethylmethoxysilane aminopropylmethyldiethoxysilane, aminopropyldimethylethoxysilane, 2-(aminoethyl)-3-aminopropyltrimethoxysilane (AEPTMS), 2-(aminoethyl)-3-aminopropyldimethoxymethylsilane, 2-(aminoethyl)-3-aminopropyldimethylmethoxysilane, 2-(aminoethyl)-3-aminopropyltriethoxysilane, 2-(aminoethyl)-3-aminopropyldiethoxymethylsilan, 2-(aminoethyl)-3-aminopropyldimethylethoxysilane, (3-trimethoxysilylpropyl)diethylenetriamine(3-dimethoxymethylsilylpropyl)diethylenetriamine, (3-dimethylmethoxysilylpropyl)diethylenetriamine, (3-triethoxysilylpropyl)diethylenetriamine (TMSPDETA), (3-diethoxymethylsilylpropyl)diethylenetriamine, (3-dimethylethoxysilylpropyl)diethylenetriamine.

The compounds may be used alone or in combination of two or more different compounds.

A further preferred class of film-forming agents forming a coating layer on the surface of the particulate filler are epoxide group containing silanes or siloxanes suitable for crosslinking with amines, mixed epoxide-amine compounds, or carboxylic acids such as polyacrylic acid.

Preferred compounds are selected from 2-(3,4-epoxycyclohexyl)ethyl triethoxy silane, 2-(3,4-epoxycyclohexyl) ethyl trimethoxy silane, (3-glycidoxypropyl)trimethoxy silane, (3-glycidoxypropyl)triethoxy silane, 5,6-epoxyhexyl triethoxy silane, (3-glycidoxypropyl)methyldiethoxy silane, (3-glycidoxypropyl)methyldimethoxy silane, and (3-glycidoxypropyl)dimethylethoxy silane.

A further preferred class of film-forming agents forming a coating layer on the surface of the particulate filler are isocyanate group containing silanes or siloxanes suitable for crosslinking with amines, isocyanate-amine mixtures, or isocyanate-diol mixtures. A preferred compound is 3-isocyanatopropyltriethoxy silane.

A further preferred class of film-forming agents forming a coating layer on the surface of the particulate filler are carboxylic acid anhydride group containing silanes or siloxanes suitable for crosslinking with amines, diols, anhydride-amine mixtures, and anhydride-diol mixtures. A preferred compound 3-(triethoxysilyl)propylsuccinic anhydride.

Moreover, the film-forming agent may comprise organically modified ceramic particles (ORMOCER) as disclosed in EP0451709.

The coating step may be carried out by mixing the film-forming agent with the dispersed particulate filler, optionally in the presence of a suitable solvent. The solvent is not particularly limited as long as the film-forming agent may be dissolved therein. Examples of suitable solvents are selected from tetrahydrofurane, 1,4-dioxane, acetone, ethanol, propanol, pentane, hexane, heptane, cyclohexane, toluene, xylene, chloroform, methylene chloride, methyl ethyl ketone, methyl isobutyl ketone, diethyl ether, tert.-butylmethyl and ether. The solvents may used alone or as a mixture of two or more liquids in amounts which are miscible with each other.

The coating composition may preferably contain film-forming compounds compounds in an amount of from 5 to 100 wt-%, preferably in an amount of from 20 to 70 wt. % based on the entire composition. According to a specific embodiment, the coating composition contains the film-forming compounds in an amount of 100 wt. %.

Preferably, the polymerizable composition has a dynamic viscosity in the range of from 0.0001 to 15 Pas (23° C.). Preferably, the thickness of the coating layer of the polymerizable monomer is less than the median particle diameter (D50) of the particulate filler.

The Coating of the Particulate Filler

The coating temperature is not particularly limited. Accordingly, the coating step may in general be carried out at a temperature of from −20° C. 250° C. In particular, the coating temperature may be in the range between 0° C. to below the boiling point of the coating composition. Preferably, the dispersion step is carried out at a temperature in the range of from 10° C. to 150° C. The dispersion may be carried out for up to 10 hours, preferably from 10 seconds to 1 hour.

High shear forces may be applied by intense mechanical stirring, ultrasonication or atomization by using a nozzle.

Subsequent to the coating step, the coated particulate filler may be isolated. The isolation may be carried out by separation of the coated particulate filler by using centrifugation or filtration.

Alternatively, any volatile components including any solvent may be separated by evaporation. The coated particulate filler may be further purified by drying at an elevated temperature of from 50° C. to 150° C. for 1 hour to 36 hours. Alternatively, the coated particles are agglomerated concurrently for forming a granulation of the coated particulate filler.

In order to eliminate particles having an undesired particle size, the coated particulate filler may be sieved prior to the agglomeration step.

The Step of Agglomerating the Coated Particulate Filler

Subsequent to or concurrent with the coating of the particulate filler, the coated particulate filler is agglomerated for providing a granulation of the coated particulate filler.

Agglomeration means that the fine coated particulate filler is dispersed either in a gas or a liquid for forming particles having a larger median particle diameter (D50) as a coarser product. The process of agglomeration is not particularly limited as long as the particle size of the granulate may be controlled by the agglomeration process.

Agglomeration may be carried out by spray agglomeration (Spray Methods), wherein a suspension of the coated particulate filler is atomized, and the liquid is evaporated from the droplets by means of hot air, as a preliminary drying step. The first cohesive forces are the capillary forces, which are followed by crystal (fluid) bridges at the contact points. Advantageously, spray agglomeration is carried out for preparing composite filler particles having a relatively small particle size.

Agglomeration may be carried out by growth agglomeration wherein fine particles are brought into contact with each other in a flowing system or in air, optionally in the presence of an additional liquid binder such as a crosslinking agent. Growth agglomeration is the growth of more or less solid agglomerates in either of two environments. The first is a rotating apparatus that produces both a mixing and a rolling motion. The second is a turbulently agitated suspension of particles that generates interparticle collisions. There is a stable accumulation if the attractive forces in the system always are greater than the destructive forces present in the system. The process may be carried out with equipment selected from inclined drums, cones, pans, paddle mixers, and plowshare mixers. Furthermore, agglomeration may also involve the use of a fluidized bed. Advantageously, growth agglomeration is carried out for preparing composite filler particles having a relatively large particle size.

During agglomeration, fluid material bridges between the coatings formed by the polymerizable composition on the surface of the particulate filler are formed. Fluid bridges may be formed by capillary forces between the particle and the polymerizable composition and optionally a further binder such as a crosslinking agent.

In case the agglomeration step is carried out in a liquid dispersion medium, the agglomeration may be carried out at a temperature of from 0° C. to the boiling point of the liquid. Preferably, the dispersion step is carried out at a temperature in the range of from 10° C. to 150° C.

The agglomeration step may be carried out by mixing the coated particulate filler optionally in the presence of a further crosslinking agent and optionally in the presence of a further particulate filler not displaying reactive groups, the presence of a suitable solvent. The solvent is not particularly limited as long as a crosslinking agent may be dispersed or dissolved therein. Examples of suitable solvents are selected from tetrahydrofurane, 1,4-dioxane, acetone, ethanol, propanol, pentane, hexane, heptane, cyclohexane, toluene, xylene, chloroform, methylene chloride, methyl ethyl ketone, methyl isobutyl ketone, diethyl ether, tert.-butylmethyl and ether. The solvents may used alone or as a mixture of two or more liquids in amounts which are miscible with each other.

The optional further particulate filler not displaying reactive groups may be selected from any of the particlulate fillers or modified particulate fillers, vide supra.

The optional further crosslinking agent may be selected from any of the film-forming agents useful for coating the particulate filler or modified particulate filler, vide supra.

In case the agglomeration step is carried out in a gaseous dispersion medium, the agglomeration may be carried out at a temperature of from −20° C. 250° C. 0° C., preferable at a temperature of from 0° C. to 100° C. More preferably, the dispersion step is carried out at a temperature in the range of from 10° C. to 40° C.

The agglomeration may be carried out for up to 10 hours, preferably from 10 seconds to 1 hour. In order to complete the crosslinking reaction, the agglomerated coated filler may be heated to an elevated temperature, preferably after the solvent has been evaporated. The composite filler particles are prepared according to the present invention by a process comprising a further step of crosslinking the granulation of the coated particulate filler for providing the composite filler particles.

Crosslinking may additionally be carried out be irradiating and/or heating the granulate. Irradiation maybe carried out by subjecting the granulate to radiation having a wavelength in the range of from 100 to 1000 nm for 1 to 60 minutes. Heating may be carried out by subjecting the granulate to a temperature of from 30 to 250° C.

Subsequent to the agglomeration step, the composite filler particles may be isolated. The isolation may be carried out by separation of the coated particulate filler by using centrifugation or filtration. Alternatively, any volatile components including any solvent may be separated by evaporation. The coated particulate filler may be further purified by drying at an elevated temperature of from 50° C. to 150° C. for 1 hour to 36 hours.

In order to adjust the particle size of the composite filler particles, the composite filler particles may be dispersed in a suitable dispersion fluid by using high shear forces such as mechanical comminution, mixing, ultrasonication, or atomization using a nozzle.

In order to eliminate particles having an undesired particle size, the coated particulate filler may be sieved prior to the agglomeration step.

The crosslinking reaction may be a chain growth polymerization and/or a step growth polymerization.

When crosslinking is carried out by chain growth polymerization, unsaturated double bonds present on the coated particulate filler in the granules react by a mechanism selected from a free radical mechanism, cationic addition polymerization and anionic addition polymerization. Accordingly, the polymerizable composition may contain a polymerization initiator and a stabilizer. Suitable radical polymerization initiators may be selected from the following classes of initiator systems:

Combinations of an organic peroxide and an amine, wherein the organic peroxide may be benzoyl peroxide or a thermally more stable peroxide such as 2,5-dimethyl-2,5-di (benzolyperoxy)hexane, tert.-butylamyl peroxide, di-(tert.-butyl) peroxide, cumene hydroperoxide, tert.-butylhydroperoxide, tert.butyl-peroxy-(3,5,5-trimethyl hexanoate), tert.-butylperoxy benzoate and tert.butylperoxy-2-ethylhexyl carbonate. The amine compound may be an aromatic amine compound such as DMABE.

Combinations of an organic peroxide, a reducing agent and a suitable metal ion. The peroxide may be selected from benzoyl peroxide, 2,5-dimethyl-2,5-di(benzolyperoxy) hexane, tert.-butylamyl peroxide, di-(tert.-butyl) peroxide, cumene hydroperoxide, tert.-butylhydroperoxide, tert.butyl-peroxy-(3,5,5-trimethyl hexanoate), tert.-butylperoxy benzoate and tert.butylperoxy-2-ethylhexyl carbonate. The reducing agent may be a protected reducing agent in inactive form, which forms an active reducing agent as disclosed in EP 0 951 894. The metal ion may be a salt of a metal or an organometalic compound, which may be present as an acetate, salicylate, naphenoate, thiourea complex, acetylacetonate or ethylene tetramine acidic acid. Suitable metal ions are selected from copper, iron, and silver.

Combinations of a hydroperoxide and a metal ion. A suitable hydroperoxide is hydrogen peroxide. A suitable metal may be selected from iron and copper.

Transition metal carbonyl compounds such as dicopper octacarbonyl complexes which may from radical species.

Alkylboron compounds such as alkyl boranes.

Combinations of peroxdisulphate salts and thiol compounds.

It is also possible to use a photoinitiator such as a camphor quinone/amine intiator.

When crosslinking is carried out by a step-growth polymerisation, a bridge between the coated particulate filler in the granules is formed by the stepwise reaction between functional groups of monomers such as by a condensation reaction or the formation of a urethane bond.

The particulate filler is agglomerated, optionally in the presence of a further crosslinking agent and optionally in the presence of a further particulate filler not displaying reactive groups, for providing a granulation of the coated particulate filler wherein the granulation contains the coated particulate filler particles separated from and connected to each other by at least one coating layer, and whereby the coating layers may be crosslinked by crosslinking groups obtained by reacting the reactive groups and optionally a further crosslinking agent The coated particulate filler may be crosslinked by using anhydride group containing crosslinking agents for crosslinking coated particulate filler particles displaying amine or hydroxyl groups on the coating layer.

A preferred group of anhydride group containing crosslinking agents are selected from 2,2-bis-(4-phthalic anhydride-4-oxyphenyl)-propane, butantetracarboxylic acid dianhydride, 4,4'-oxybis-phthalic acid anhydride, benzophenone-3,3',4,4'-tetracarboxylic acid dianhydride, biphenyl-3, 3',4,4'-tetracarboxylic acid dianhydride, pyromellitic acid dianhydride, poly(ethylene-alt-maleic acid anhydride).

A further class of crosslinking agent is a polyisocyanate crosslinking agent for crosslinking coated particulate filler particles displaying amine or hydroxyl groups on the coating layer. Preferred polyisocyanate crosslinking agents are selected from the group of 1,3-bis-(1-isocyanato-1-methylethyl)benzene, 1,3-bis-(isocyanatomethyl)-cyclohexane, hexamethylene diisocyanate, toluene-2,4-diisocyanate, trimethylhexamethylene diisocyanate, methylene di(phenylisocyanate), 4,4'-diisocyanatodicyclohexyl methane, and isophorone diisocyanate.

A further class of crosslinking agents are epoxide crosslinking agents for crosslinking coated particulate filler particles displaying amine groups on the coating layer. Preferred epoxide crosslinking agents are selected from 1,4-cyclohexane dimethanol-diglycidyl-ether, 1,4-butanedioldiglycidyl ether, bisphenol-F diglycidyl ether, isocyanuric acid tris-(2,3-epoxypropyl) ester, neopentylglycol diglycidyl ether, triphenylolmethan triglycidyl ether, and bisphenol-A diglycidyl ether.

A further class of crosslinking agents are amine crosslinking agents for crosslinking coated particulate filler particles displaying isocyanate groups, epoxide groups, or anhydride groups on the coating layer. Preferred amine crosslinking agents are selected from ethylene diamine, 1,3-propane diamine, diethylene triamine, triethylene tetraamine, and tetraethylene pentamine, aminoethyl piperazine, polyether amines such as 4,7,10-trioxa-1,13-tridecane diamine 2,2'-ethylendioxy) diethylamine, 1,3-bis-(aminomethyl) cyclohexane, 1,3-bis-(4-aminophenoxy)benzene, 4,4'-methylene bis-cyclohexylamine, 5-amino-1,3,3-trimethyl-cyclohexanemethylamine, 3,(4),8,(9)-bis(aminomethyl)-tricyclo-5.2.1.0 (2,6)-decane.

A further class of crosslinking agents are hydroxyl group containing crosslinking agents for crosslinking coated particulate filler particles displaying isocyanate groups, epoxide groups and anhydride groups. Preferred hydroxyl group containing crosslinking agents are selected from polyols (e.g. Desmophen® Polyetherpolyol), 1,3-propane diol, ethylene glycol, diethylene glycol, triethylene glycol.

The above crosslinking agents may be used alone or in combination.

Now the present invention will be described to generic embodiments.

FIG. 1 is a flow chart illustrating a first generic embodiment of the process for the preparation of a composite filler particles of the present invention based on a suspension/emulsion technique. Accordingly, the surface of a particulate filler is modified prior to the coating step by silanation. A suitable silanating agent is 3-methacryloylpropyl trimethoxysilane. Subsequently, the particulate filler is coated with a coating composition containing a film-forming agent forming a coating layer on the surface of the particulate filler. A suitable coating composition may contain a silanation agent having reactive groups such as amino groups, carboxylic acid anhydride groups, isocyanate groups or epoxy groups. The coating composition may optionally contain a reactive diluent and or a solvent. Accordingly, a coated particular filler is provided wherein said coating layer displays reactive groups on the surface of the coating layer. Subsequently, the coated particulate filler is agglomerated by emulsification or suspension of the mixture in a solvent wherein neither the particles nor the coating composition are soluble. Accordingly, a granulation of the coated particulate filler is provided wherein the granulation contains the coated particulate filler particles and the optional further particulate filler particles separated from and connected to each other by at least one coating layer. Subsequently, polymerization and crosslinking of the reactive groups displayed on the coated particles is carried out, whereby the at least one coating layer is crosslinked by crosslinking groups obtained by reacting the reactive groups the coated particulate filler. According to the first generic embodiment, composite filler particles may be provided which have a median particle size (D50) of from 1 to 70 μm, wherein reactive groups are transformed into crosslinking groups obtained by reacting reactive groups and optionally a further crosslinking agent, and wherein the particulate filler is the main component by volume of the composite filler particles.

Figure 2:
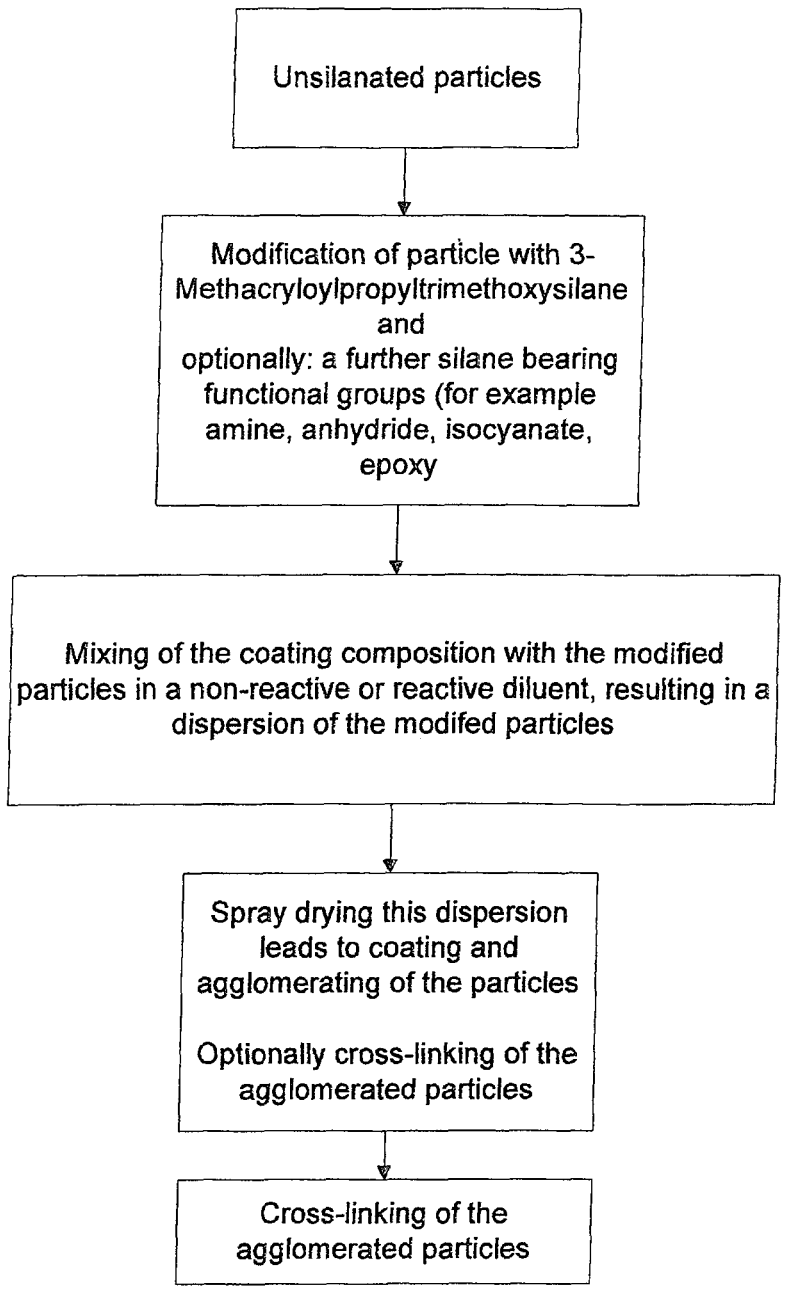
FIG. 2 is a flow chart illustrating a second generic embodiment of the process of the present invention wherein a spray dryer is used.

FIG. 2 is a flow chart illustrating a second generic embodiment of the process for the preparation of composite filler particles of the present invention wherein a spray dryer is used. Accordingly, the surface of a particulate filler is modified prior to the coating step by silanation. A suitable silanating agent is 3-methacryloylpropyl trimethoxysilane. Subsequently, the modified particles are mixed with a coating composition whereby a dispersion of the modified particles is obtained. The dispersion of the modified articles in the coating composition is then spray dried by using a spray dryer whereby the particles are agglomerated. Accordingly, the coating of the particulate filler and the agglomeration of the coated particulate filler takes place concurrently. The spray dried product may be heat treated for reacting the reactive groups and optionally a further crosslinking agent and to provide crosslinking groups. According to the second generic embodiment, composite filler particles may be provided which have a median particle size (D50) of from 1 to 70 μm, wherein reactive groups are transformed into crosslinking groups obtained by reacting reactive groups and optionally a further crosslinking agent, and wherein the particulate filler is the main component by volume of the composite filler particles.

Figure 3:
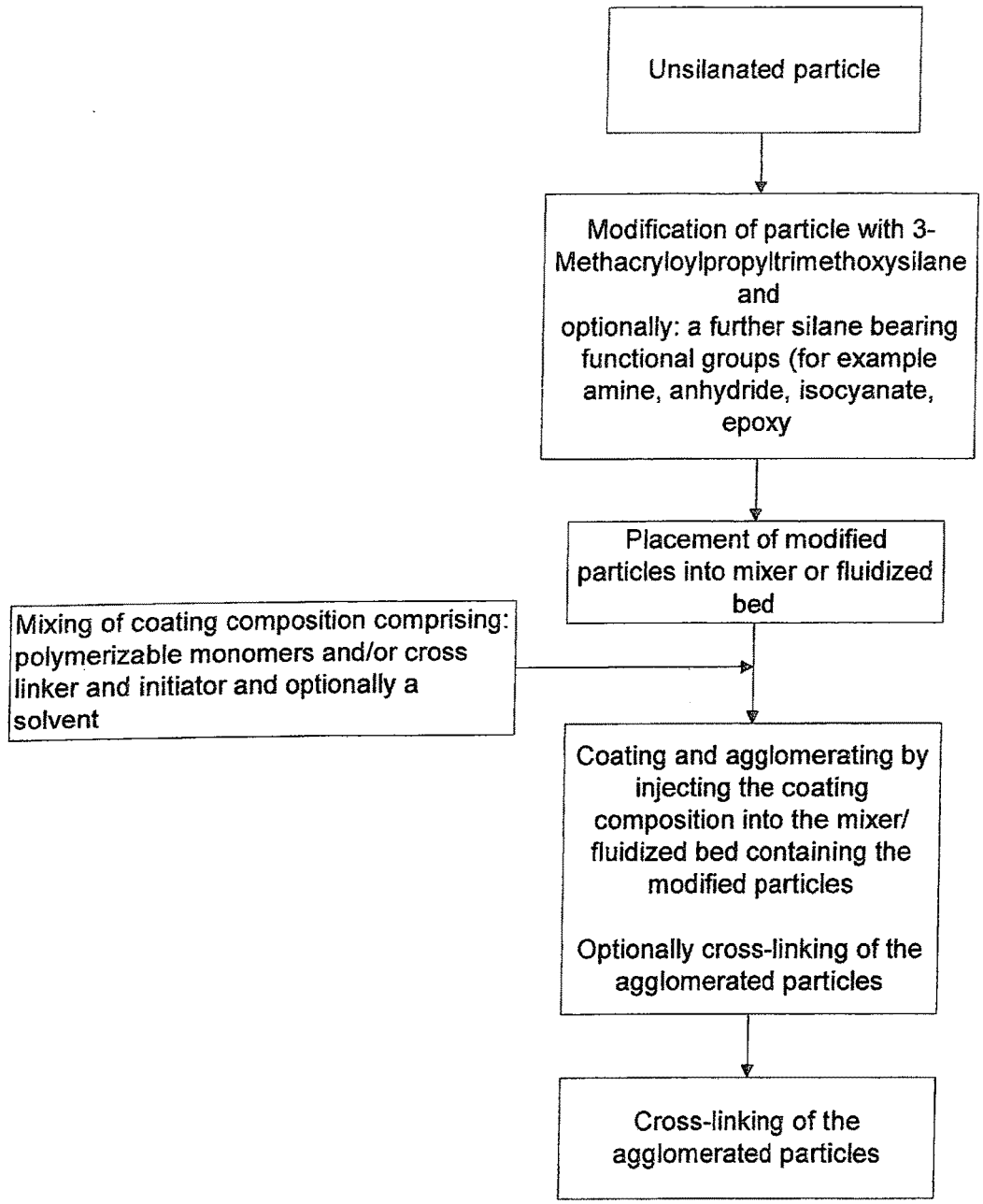
FIG. 3 is a flow chart illustrating a third generic embodiment of the process of the present invention based on wherein a high shear mixer or a fluidized bed is used.

FIG. 3 is a flow chart illustrating a third generic embodiment of the process of the present invention based on wherein a high shear mixer or a fluidized bed is used. Accordingly, the surface of a particulate filler is modified prior to the coating step by silanation. A suitable silanating agent is 3-methacryloylpropyl trimethoxysilane. Subsequently, the particulate filler is coated with a coating composition containing a film-forming agent forming a coating layer on the surface of the particulate filler and concurrently agglomerated in a high shear mixer or a fluidized bed. A suitable coating composition may contain a silanation agent having reactive groups such as amino groups, carboxylic acid anhydride groups, isocyanate groups or epoxy groups. The coating composition may optionally contain a reactive diluent and or a solvent. Accordingly, an agglomerated coated particular filler is provided wherein said coating layer displays reactive groups on the surface of the coating layer, and wherein the coated particulate filler is agglomerated. The granulation of the coated particulate filler is provided wherein the granulation contains the coated particulate filler particles and the optional further particulate filler particles separated from and connected to each other by at least one coating layer. Subsequently, polymerization and crosslinking of the reactive groups displayed on the coated particles is carried out, whereby the at least one coating layer is crosslinked by crosslinking groups obtained by reacting the reactive groups the coated particulate filler. According to the third generic embodiment composite filler particles may be provided which have a median particle size (D50) of from 1 to 70 μm, wherein reactive groups are transformed into crosslinking groups obtained by reacting reactive groups and optionally a further crosslinking agent, and wherein the particulate filler is the main component by volume of the composite filler particles.

The Dental Composition

The composite filler particles of the present invention may be used for the preparation of a dental composition. A dental composition is preferably a dental restorative material. The dental restorative material may be selected from a dental composite, a dental cement or a resin reinforced dental cement. A dental composite may be a highly filled dental composite, a flowable composite, a compomer, a root canal sealer, or a pit and fissure sealant. A dental cement may be a glass ionomer cement or a luting cement.

A dental composite contains the particulate composite filler of the present invention and a polymerizable monomer, a polymerization initiator, and optionally an additional filler. According to a preferred embodiment, the additional filler may be a particulate filler or surface-modified particulate filler as used for the preparation of the composite particulate filler of the present invention.

In case of a particulate composite filler for use in a dental cement, the polymerizable compound may also be a modified polyacid having polymerizable double bonds.

It is possible to use a combination of both types of polymerisations for providing a resin reinforced dental cement.

The polymerizable monomer is preferable a compound having at least one polymerizable group. Generally in dental compositions, radical polymerization is performed. Therefore, the polymerizable group is typically a radical polymerizable group. As the polymerizable group, (meth)acryloylamino or a (meth)acryloyloxy group, is preferable. The polymerizable monomers may be selected from the same polymerisable compounds as contained in the polymerisable composition used for coating the particulate filler.

The additional filler includes glass particles such as barium aluminum-borosilicate glass, barium aluminofluorosilicate glass and mixtures thereof. In these materials, barium can also be substituted by strontium, and may also contain fluoride. Other useful materials include calcium hydroxy ceramics, and others such as those fillers disclosed in U.S. Pat. Nos. 5,338,773, 5,710,194, 4,758,612, 5,079,277, and 4,814,362. These materials may have any morphology or shape, including spheres, regular or irregular shapes, filaments or whiskers, and the like and silane treated (silane coupled) or provided with other treatments as is conventional for dental fillers.

The initiator may be any thermal initiator or photoinitiator conventionally used in the dental field. A dental composite may, furthermore, contain inhibitors, UV absorbers, accelerators, or fluorescing agents.

A dental cement is usually powder liquid systems consisting of linear poly(alkenoic acid)s and reactive ion releasing active glasses. The most common poly(alkenoic acid)s are polymers such as polyacrylic acid or copolymers of acrylic and itaconic acid, acrylic acid and maleic acid and to some degree a copolymer of acrylic acid with methacrylic acid. In the presence of water, the poly(alkenoic acid) attacks the glass powder whereby metal ions such as calcium, aluminum and strontium are released under formation of intra- and intermolecular salt bridges which crosslink the composition. The particulate composite filler of the present invention may be incorporated into dental cement either as an unreactive glass filler or as a reactive glass filler.

EXAMPLES

The present invention will now be explained in further detail with reference to the following examples.

According to the present invention, the median particle size (D50) of the composite filler particles is measured according to the following procedure:

2 g of the particles are added to 4 mL of ethanol and 2 drops of Tween 85® are added. The particles are predispersed by shaking the mixture until a visibly homogeneous mixture is achieved. Subsequently, the mixture is added into the measuring cell of a Malvern Mastersizer S, containing 800 mL of water and being equipped with a stirrer set to 2200 and an ultrasound probe set to 1800, while stirring the dispersion until an turbidity of approx. 20-25% was reached. The median particle size (D50) is measured after applying ultrasound from the ultrasound probe in the measurement cell under stirring for 10 Minutes. Ultrasound is applied to break up loosely aggregated particles and to distinguish them from the agglomerated particles.

Example 1—Coating of a Particulate Filler 112.5 g of a strontium-aluminum-sodium-fluoride-phosphorous-silicate glass having a particle size D50=0.7 µm are dispersed in 200 mL ethanol at room temperature for 15 minutes in an ultrasound bath. 1.6 mL (1.6 g) (3-aminopropyl)trimethoxysilane dissolved in 10 mL ethanol, and 1.5 mL (1.4 g) 3-(trimethoxysilyl)propylmethacrylat, dissolved in 10 mL ethanol are added simultaneously to the glass suspension. During the addition, suspension is treated with ultrasound. After the addition is complete, the suspension is treated for additional 30 minutes with ultrasound at room temperature. Subsequently, the solvent is removed in vacuo and the residue is dried for 24 h at 100° C. for providing a coated particulate filler. The coated particulate filler is the sieved by using a 180 µm sieve. The median particle size D50 of the coated particulate filler was determined to be D50=0.74 µm.

In a beaker containing about 50 mL water, a portion of about 50 mg of the coated particulate filler is placed on the surface whereby the coated particulate filler stays afloat, which indicates that the particulate filler has been coated with hydrophobic 3-(trimethoxysilyl)propyl methacrylate.

20 mg of the coated particulate filler are placed on a thin layer chromatography plate and treated with a solution of ninhydrin (0.5 g ninhydrin in 100 mL ethanol) and heated whereby a blue color appears which indicates the presence of amino groups.

Example 2—Aggregation of Coated Particulate Filler 70 mg isophoren diamine (5-amino-1,3,3-trimethylcyclohexanemethylamine) are dissolved in 2.5 mL tetrahydrofuran (THF). 280 mg bisphenol-A-diglycidyl ether are dissolved in 2.5 mL THF. Both solutions are mixed with 5.00 g of the coated particulate filler and the solvent is removed in vacuo (50 mbar) at 30° C. The resulting granulation of the coated particulate filler is kept in a sealed container for 5 hours at 70° C. Subsequently, about 1.5 g of the resulting granulation is added to 10 mL of ethanol and treated for 1 h with ultrasound. The median particle size of the composite filler particles was determined to be D50=3.3 µm.

Example 3—Aggregation of Coated Particulate Filler 77 mg TCD-diamin (3(4),8(9)-Bis-(aminomethyl)-tricyclo[5.2.1.02,6]decan) are dissolved in 2.5 mL THF. 280 mg bisphenol-A-diglycidyl ether are dissolved in 2.5 mL THF. Both solutions are mixed with 5.00 g of the coated particulate filler and the solvent is removed in vacuo (50 mbar) at 30° C. The resulting granulation of the coated particulate filler is kept in a sealed container for 5 hours at 70° C. Subsequently, about 1.5 g of the resulting granulation is added to 10 mL of ethanol and treated for 1 h with ultrasound. The median particle size of the composite filler particles was determined to be D50=4.5 µm.

Example 4—Agglomeration Using a Büchi Mini Spray Dryer (Büchi Minispruhtrockner B-290)

100 g of modified particles (median particle size D50=1.2 µm) (modified with 1.5 wt.-% 3-Methacryloylpropyltrimethoxysilane and 1.5 wt.-% 3-Aminopropyltrimethoxysilane) were mixed with a defined amount of acetone (see table 1) using a magnetic stirrer. Epilox (CAS 1675-54-3) and TCD diamine (CAS 68889-71-4) (see table 1) were added to this mixture. The mixture was then injected into the spray dryer using its internal peristaltic pump and a 2 component jet nozzle from Büchi (nozzle diameter=1.4 mm) (pump rate see table 1). The aspirator efficiency was set to 100%. The process parameters used are listed in table 1.

After the agglomerated particles were spray dried, the agglomerated particles were sieved through a 300 µm sieve and dried for 24 hours at 80° C. and the median particle size (D50) measured according to the procedure described before. The median particle sizes (D50) of the agglomerated particles are listed in table 1 below.

TABLE 1

List of variable amounts of Epilox and TCD diamine - variable process parameters and resulting median particle size (D50)

| Example (Experiment) | Amount epilox g | Amount TCD g | Amount acetone g | Air flow (Rotameter) mm | Pump rate % | Inlet temperature °C. | Median particle size of agglomerated particles (D50) μm |
|---|---|---|---|---|---|---|---|
| 4-1 SNO-01-15-01 | 8.44 | 1.56 | 65.20 | 50 | 40 | 130 | 15.2 |
| 4-2 SNO-01-16-01 | 12.35 | 2.65 | 78.60 | 40 | 20 | 100 | 20.0 |
| 4-3 SNO-01-19-01 | 12.35 | 2.65 | 54.42 | 40 | 20 | 160 | 36.4 |
| 4-4 SNO-01-20-01 | 4.53 | 0.47 | 80.26 | 60 | 20 | 100 | 8.8 |
| 4-5 SNO-01-27-01 | 12.35 | 2.65 | 78.60 | 60 | 60 | 100 | 52.6 |

Example 5—Agglomeration Using a High Shear Mixer (Diosna Laboratory Mixer P1-6)

450 g of modified particles (median particle size D50=1.2 μm) (modified with 1.5 wt.-% 3-Methacryloylpropyltrimethoxysilane and 1.5 wt.-% 3-Am inopropyltrimethoxysilane) were placed into the mixer. Separately, a defined amount of Epilox (CAS 1675-54-3) was dissolved in acetone (see table 2) and TCD diamine (68889-71-4) added to this mixture (see table 2). This mixture was then injected into the mixer using a 2 component Schlick jet nozzle (model 970/7, nozzle size 0.8 mm) and a Watson Marlow D323 peristaltic pump. During the injection process, the particles were mixed using a 3 wing impeller and a chopper at defined rpm (see table 2). The pressure applied to the jet nozzle as well as the pump speed in rpm is listed in table 2. After the complete addition, the obtained powder might be subjected to an additional mixing step (see table 2). After the mixing was complete, the agglomerated particles were sieved through a 300 μm sieve and dried for 24 hours at 80° C. and the median particle size (D50) measured according to the procedure described before. The median particle sizes (D50) of the agglomerated particles are listed in Table 2 below.

Example 6—Agglomeration Using a High Shear Mixer (Diosna Laboratory Mixer P1-6)

450 g of modified particles (median particle size D50=1.0 μm) (modified with 3.1 wt.-% 3-Methacryloylpropyltrimethoxysilane) were placed into the mixer. Separately, a defined amount of ethoxylated bisphenol-A-dimethacrylate (EBA) (CAS 41637-38-1) was mixed with a defined amount of trimethylolpropane trimethacrylate (TMPTMA) (3290-92-4) and a defined amount of tert-butylperoxy 2-ethylhexylcarbonate (TBPEHC) (CAS 34443-12-4) (see table 3) using a magnetic stirrer until a visually homogeneous mixture was achieved. This mixture was then injected into the mixer using a 2 component Schlick jet nozzle (model 970/7, nozzle size 0.8 mm) and a Watson Marlow D323 peristaltic pump. During the injection process, the particles were mixed using a 3 wing impeller and a chopper at defined rpm (see table 3). The pressure applied to the jet nozzle was set to 0.3 bar, while the applied pump speed in rpm is listed in table 3. After the complete addition, the obtained powder was subjected to an additional mixing step for 60 seconds using the same parameters for the impeller and chopper rpm. After the mixing was complete, the agglomerated particles were sieved through a 300 μm sieve and dried for 24 hours at 80°

TABLE 2

List of variable amounts of Epilox and TCD diamine - variable process parameters and resulting median particle size (D50)

| Example (Experiment) | Amount epilox g | Amount TCD g | Amount acetone g | Impeller speed rpm | Chopper speed rpm | Pressure applied to jet nozzle bar | Additional mixing sec | Pump speed rpm | Median particle size of agglomerated particles (D50) μm |
|---|---|---|---|---|---|---|---|---|---|
| 5-1 KJ18-182-2 | 37.99 | 7.01 | 45.00 | 500 | 1600 | 0.5 | 60 | 38 | 45.3 |
| 5-2 KJ-18-182-15 | 20.39 | 2.11 | 22.50 | 250 | 2200 | 0.7 | 120 | 17 | 11.3 |
| 5-3 KJ-18-182-11 | 20.39 | 2.11 | 22.50 | 750 | 1000 | 0.7 | 120 | 17 | 5.7 |
| 5-4 KJ-18-182-18 | 20.39 | 2.11 | 22.50 | 250 | 1000 | 0.3 | 120 | 17 | 12.7 |
| 5-5 KJ-18-182-14 | 20.39 | 2.11 | 22.50 | 750 | 1000 | 0.3 | 0 | 17 | 6.2 |

C. and the median particle size (D50) measured according to the procedure described before. The median particle sizes (D50) of the agglomerated particles are listed in table 3 below.

TABLE 3

List of variable amounts of EBA, TMPTMA and TBPEHC - variable process parameters and resulting median particle size (D50)

| Example (Experiment) | Amount EBA g | Amount TMPTMA g | Amount TBPEHC g | Impeller speed rpm | Chopper speed rpm | Pump speed rpm | Median particle size of agglomerated particles (D50) µm |
|---|---|---|---|---|---|---|---|
| 6-1 SST-02-33-01 | 15.75 | 15.75 | 0.50 | 250 | 1500 | 20 | 3.1 |
| 6-2 SST-02-33-02 | 33.75 | 11.25 | 0.90 | 200 | 2000 | 15 | 11.5 |
| 6-3 SST-02-34-01 | 10.13 | 3.38 | 0.27 | 150 | 2000 | 15 | 2.2 |
| 6-4 SST-02-34-02 | 15.75 | 15.75 | 0.50 | 200 | 2000 | 20 | 3.4 |
| 6-5 SST-02-35-02 | 23.63 | 7.88 | 1.00 | 200 | 2000 | 20 | 4.1 |

Example 7—Measurement of the Median Particle Size ($d_{50}$) of the Agglomerated Particles 2 g of the agglomerated particles were added to 4 mL of Ethanol and optionally 2 drops of Tween 85 were added. The agglomerated particles were pre-dispersed by shaking this mixture until a visible homogeneous mixture was achieved. This mixture was then added into the measuring cell of a Malvern Mastersizer S, containing 800 mL of water and being equipped with a stirrer set to 2200 and an ultrasound probe set to 1800, while stirring the dispersion until an obscuration of approx. 20-25% was reached. The median particle size ($d_{50}$) was measured after having applied ultrasound from the ultrasound probe in the measurement cell under stirring for 10 Minutes. Ultrasound was applied to deaggregate loosely aggregated particles and to distinguish them from the agglomerated particles (particles cross linked by added monomers).

Example 8—Determination of the Degree of Polymerization of the Monomers by Measuring the Amount of Extractable Monomers Method 1:
Up to 1.0 g of the dried and sieved particles was placed in a glass vessel and 10.0 g of acetonitrile were added. The mixture was placed on a laboratory shaker for 1 hour to extract leachable monomers. After 1 hour, the particles were separated by filtration and the resulting clear liquid was directly injected into the HPLC. Measurement in regard to standard solutions, containing defined amount of Ethoxylated Bisphenol A dimethacrylate (EBA) CAS: 41637-38-1 were conducted to determine the amount of extractable EBA. The amount of extractable monomers was calculated from the amount of extractable EBA. The degree of polymerization of monomers represents the amount of non extractable monomers in relation to the initial amount of monomers used for granulation.
Method 2:
7.5 g of the dried and sieved particles were placed in a centrifugation tube and 30 mL of acetone were added. The mixture was put on a laboratory shaker for 20 minutes and then centrifuged for 30 minutes at 5000 rpm. The clear supernatant was isolated by decantation. The extraction procedure (adding acetone, shaking, centrifugation and decantation) was repeated 2 times with 30 ml acetone each.

The decanted solutions were collected and combined, and the solvent removed by distillation at 40° C. and 50 mbar. The remaining residue was analyzed gravimetrically and represents the amount of extractable monomers. The measurement was conducted twice. The degree of polymerization of monomers represents the amount of non extractable monomers in relation to the initial amount of monomers used for granulation.

Example 9—Scanning Electron Microscopy Pictures

Scanning electron microscopy (SEM) pictures were taken using a Ultra high resolution FESEM from Zeiss.

Example 10—Agglomeration/Granulation Using a Büchi Mini Spray Dryer (Büchi Minisprühtrockner B-290)

A certain amount of modified particles (strontium aluminum silicate glass or barium aluminum borosilicate glass—median particle size $d_{50,3}$ and amount see table—modified with 3.1 wt.-% 3-Methacryloylpropyltrimethoxysilane CAS: 2530-85-0) were mixed with a defined amount of acetone (see table 4) using a magnetic or mechanical stirrer. A mixture of polymerizable methacrylate monomers (e.g. the monomer mixture of the commercially available material Dyract® eXtra, comprising urethane dimethacrylate, carboxylic acid modified dimethacrylate, Triethyleneglycol dimethacrylate, Trimethacrylate resin, dimethacrylate resin, campherquinone, ethyl-4(dimethylamino)benzoate, butylated hydroxyl toluene, UV stabilizer, see table 4) were added to this mixture together with a radical initiator WAKO V-601 (CAS: 2589-57-3). The mixture was homogenized by stirring and then injected into the spray dryer using its internal peristaltic pump and a 2 component jet nozzle from Büchi (nozzle diameter=1.4 mm) (process parameters see table 1). The aspirator efficiency was set to 100%. The process parameters used are listed in table 4. For all experiments, nitrogen was used as the carrier gas (drying and atomization gas).

Figure 4:
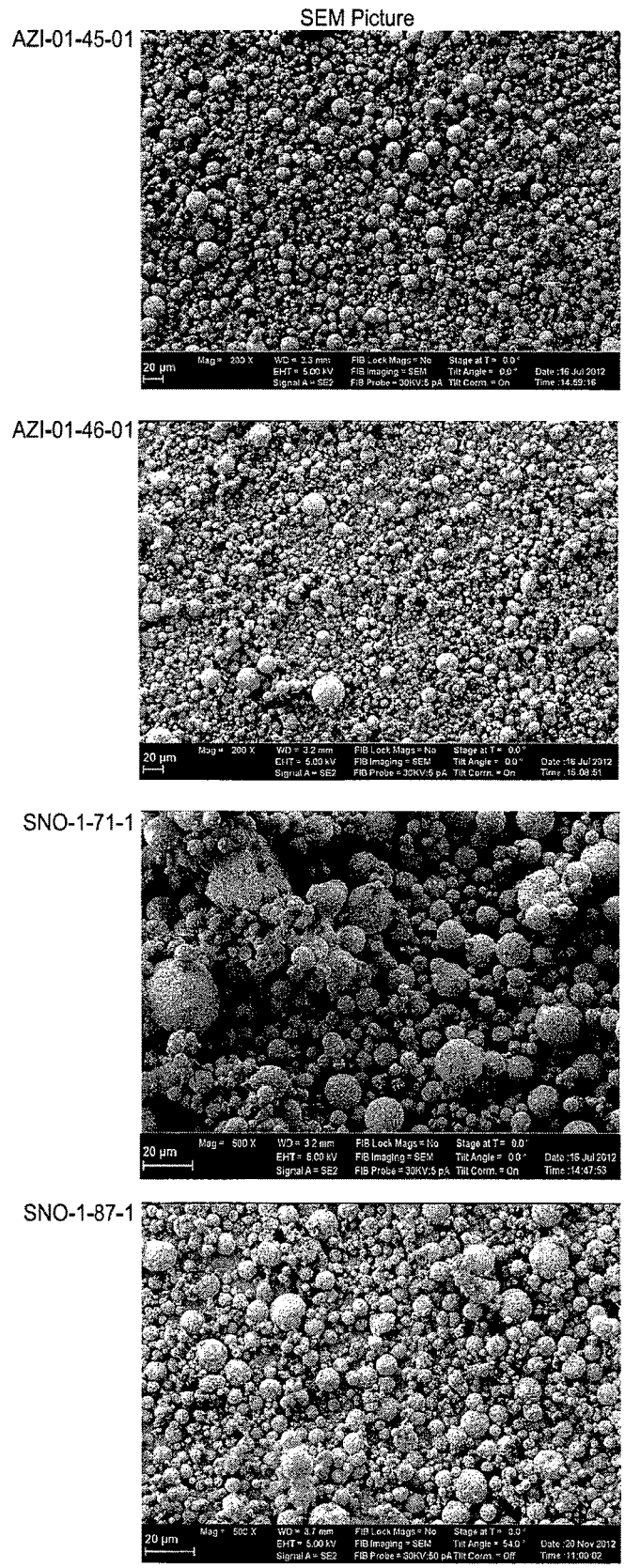
FIG. 4 shows SEM images of agglomerated fillers according to the present invention.

After the agglomerated particles were spray dried, the agglomerated particles were collected and placed in a three necked round bottom flask. The flask was purged with argon gas for at least 5 minutes and tightly sealed. The flask was put in an oven at 100° C. for 3.3 hours. The obtained particles were then sieved through a 180 μm sieve and the median particle size ($d_{50,3}$) measured according to the procedure described before. The median particle sizes ($d_{50,3}$) of the agglomerated particles are listed in table 4. The degree of polymerization of the monomers was determined using the above mentioned methods 1 or 2. SEM pictures of the agglomerated fillers are shown in FIG. 4:

TABLE 4

List of variable amounts of modified particles, monomer mixture, variable process parameters, resulting median particle size ($d_{50}$) and degree of polymerization of monomers

| Experiment | Amount modified glass filler/g | $d_{50,3}$/ μm | Total amount of monomers/ g | Amount acetone/ g | Amount Wako V-601/g | Pump rate/ % | Nozzle diameter/ mm | Air flow (Rotameter)/ mm | Inlet temperature/ ° C. | Yield/ % | Median particle size of agglomerated particles ($d_{50}$)/μm | Span of particle size distribution | Degree of polymerization of monomers/ % |
|---|---|---|---|---|---|---|---|---|---|---|---|---|---|
| AZI-01-45-01 | 250 | 0.6 | 37.5[3] | 140.2 | 0.43 | 60 | 1.4 | 50 | 120 | 91 | 12.67 ± 0.51 | 3.21 | 91[1] |
| AZI-01-46-01 | 350 | 0.6 | 35.0[3] | 210.1 | 0.40 | 60 | 1.4 | 50 | 120 | 94 | 10.66 ± 0.13 | 3.60 | 88[1] |
| SNO-1-71-1 | 350 | 0.6 | 70.0[3] | 182.5 | 0.80 | 60 | 1.4 | 50 | 120 | 91 | 29.02 ± 8.93 | 3.41 | 92[2] |
| AZI-01-58-01 | 300 | 0.6 | 45.0[3] | 168.3 | 0.51 | 50 | 0.7 | 50 | 120 | 91 | 9.79 ± 0.20 | 3.07 | 89[2] |
| AZI-01-59-01 | 300 | 0.6 | 45.0[3] | 168.3 | 0.51 | 50 | 0.7 | 50 | 120 | 91 | 9.74 ± 0.48 | 3.62 | 89[2] |
| SNO-1-87-01 | 150 | 0.5 | 22.5[4] | 153.7 | 0.25 | 60 | 1.4 | 50 | 110 | 90 | 8.05 ± 0.39 | 2.26 | 93[1] |
| AZI-01-136-01 | 300 | 0.5 | 44.8[4] | 307.5 | 0.51 | 60 | 1.4 | 50 | 110 | 94 | 9.08 ± 0.24 | 4.21 | Not determined |

[1] Method 1
[2] Method 2
[3] mixture of the commercially available material Dyract® eXtra, comprising urethane dimethacrylate, carboxylic acid modified dimethacrylate, Triethyleneglycol dimethacrylate, Trimethacrylate resin, dimethacrylate resin, campherquinone, ethyl-4(dimethylamino)benzoate, butylated hydroxyl toluene, UV stabilizer
[4] mixture of ethoxylated Bisphenol-A-dimethacrylate, urethane dimethacrylate, Trimethacrylate resin, ethyl-4(dimethylamino)benzoate

Example 11—Paste Preparation Using Agglomerated Filler

Pastes were produced by placing a mixture of polymerizable methacrylate monomers (e.g. the monomer mixture of the commercially available material Dyract® eXtra, comprising urethane dimethacrylate, carboxylic acid modified dimethacrylate, Triethyleneglycol dimethacrylate, Trimethacrylate resin, dimethacrylate resin, campherquinone, ethyl-4(dimethylamino)benzoate, butylated hydroxyl toluene, UV stabilizer; or the monomer mixture of the commercially available material Ceram.X, comprising methacrylate modified polysiloxane, dimethacrylate resins, fluorescent pigment, UV stabilizer, stabilizer, campherquinone, ethyl-4 (dimethylamino)benzoate) in an IKA laboratory kneader and adding a certain amount of a mixture of granulated filler and a further filler (see table 3) in portions under kneading to the resulting mixture. After the complete addition of the filler, further kneading steps were applied to ensure suitable distribution of the filler within the final formulation.

TABLE 5

Formulation analysis

| Experiment | Filler 1: granulated filler | Filler 2[1]: | | | Filler content | Consistency[4] | | Stickiness[5] Number of adhesive breaks | Shrinkage[6] | Flexural strength[7] |
| | | | wt.-% | wt.-% | $d_{50}$ [μm] | wt.-% | 23° C. mm | 37° C. mm | | % | MPa |
|---|---|---|---|---|---|---|---|---|---|---|---|
| AZI-01-51-01 | SNO-1-71-1 | | 60 | 40[3] | 0.6 | 76.8 | 31 | 36 | 0 | 2.4 | 90 |
| AZI-01-54-01 | AZI-01-45-01 | | 45 | 55[3] | 0.6 | 76.8 | 25 | 32 | 0 | 2.5 | 102 |
| AZI-01-49-01 | AZI-01-46-01 | | 60 | 40[3] | 0.6 | 76.8 | 14 | 21 | 6 | 2.6 | 91 |
| KJ-19-123-1 | SNO-1-71-1 | | 30 | 70[3] | 0.6 | 76.8 | 25 | 31 | 0 | 2.5 | 108 |
| KJ-19-121-1 | AZI-01-46-01 | | 30 | 70[3] | 0.6 | 76.8 | 21 | 26 | 0 | 2.6 | 126 |
| KJ-19-141-1 | — | | 0 | 100[3] | 0.6 | 76.1 | 20 | 27 | 0 | 2.7 | 117 |
| KJ-19-137-1 | AZI-01-58-01 AZI-01-59-01[2] | | 50 | 50[3] | 0.6 | 78.4 | 20 | 28 | 6 | 2.3 | 105 |
| AZI-01-68-01 | AZI-01-58-01 AZI-01-59-01[2] | | 40 | 60[3] | 0.6 | 77.8 | 22 | 29 | 5 | 2.4 | 111 |

TABLE 5-continued

Formulation analysis

| Experiment | Filler 1: granulated filler | | Filler 2[1]: | | Filler content | Consistency[4] | | Stickiness[5] Number of adhesive | Shrinkage[6] | Flexural strength[7] |
|---|---|---|---|---|---|---|---|---|---|---|
| | | wt.-% | | wt.-% | $d_{50}$ [μm] | wt.-% | 23° C. mm | 37° C. mm | breaks | % | MPa |
| AZI-01-69-01 | AZI-01-58-01 AZI-01-59-01[2] | 60 | 40[3] | 0.6 | 77.7 | 21 | 37 | 6 | 2.3 | 108 |
| KJ-19-183-01 | SNO-1-87-01 | 50 | 50 | 0.5 | 73.8 | 18 | 21 | 6 | 2.0 | 94 |

[1]same filler used to generate granulated filler table 1
[2]a 1:1 mixture of AZI-01-58-01 and AZI-01-59-01 was used
[3]Filler 1 and Filler 2 were mixed prior to addition to formulation using a Willy A. Bachofen Turbula T2F at 50 rpm for 10 minutes
[4]Determined by placing a weight of approx. 575 g on a specimen with a volume of 0.5 mL (D7.0 mm) for 120 seconds at 23° C. or 37° C., and measure diameter of the resulting round round disk in mm.
[5]Determined using a by placing the material between two metal plates (one fixed lower plate, one movable upper plate). The distance between both plates is set to 2 mm. After annealing the material to 35° C. for 5 minutes, the upper plate is retracted at a constant speed (approx.. 1 mm/s) and the breakage of the material is observed. A break of the material, during retraction of the upper plate) within the material itself constitutes a cohesive break, while a breakage of the material from either plate constitutes an adhesive break. A total of 6 measurements was made. A high number of adhesive breaks (maximum 6 out of 6) shows a low stickiness of the material.
[6]Determined by measuring the change in density before and after polymerization and calculating the volumetric shrinkage using the Archimedes hydrostatic uplift principle
[7]Determined according to ISO 4049:2009

Comparative Example 1—U.S. Pat. No. 4,781,940 "Method for Producing Filler for Microfilled Dental Composite Material"

According to Example 1 of U.S. Pat. No. 4,781,940 disclosing the preparation of a filler for a dental composite material, one hundred grams of OX-50 silica that had been treated with 5%, by weight, of A-174 silane is placed in a mixing vessel with a solution containing 120 grams of methylene chloride and 25 grams of the following monomer mixture containing 61.8 wt.-% bis-GMA, 6.9 wt.-% bisphenol-A dimethacrylate, 29.4 wt.-% triethylene glycol dimethacrylate and 2.0 wt.-% radical initiator.

The slurry is poured into a tray and the methylene chloride is evaporated by allowing the tray and its contents to stand in air at ambient temperature (about 23° C.) for 16 hours.

After evaporating the methylene chloride solvent, the coated silica is then passed through a 165 mesh screen. The sieved material is heated to 120° C. for 4 hours in a vacuum oven under a vacuum of 30 mm Hg (absolute pressure).

After the heating step, the powder is cooled, sieved again through a 100 μm sieve. The sieved material was heated to 120° C. for 4 hours in a vacuum oven, or alternatively in an inert atmosphere. After heating, the material was sieved again through a 100 μm sieve for providing the filler for a dental composite material.

Figure 5:
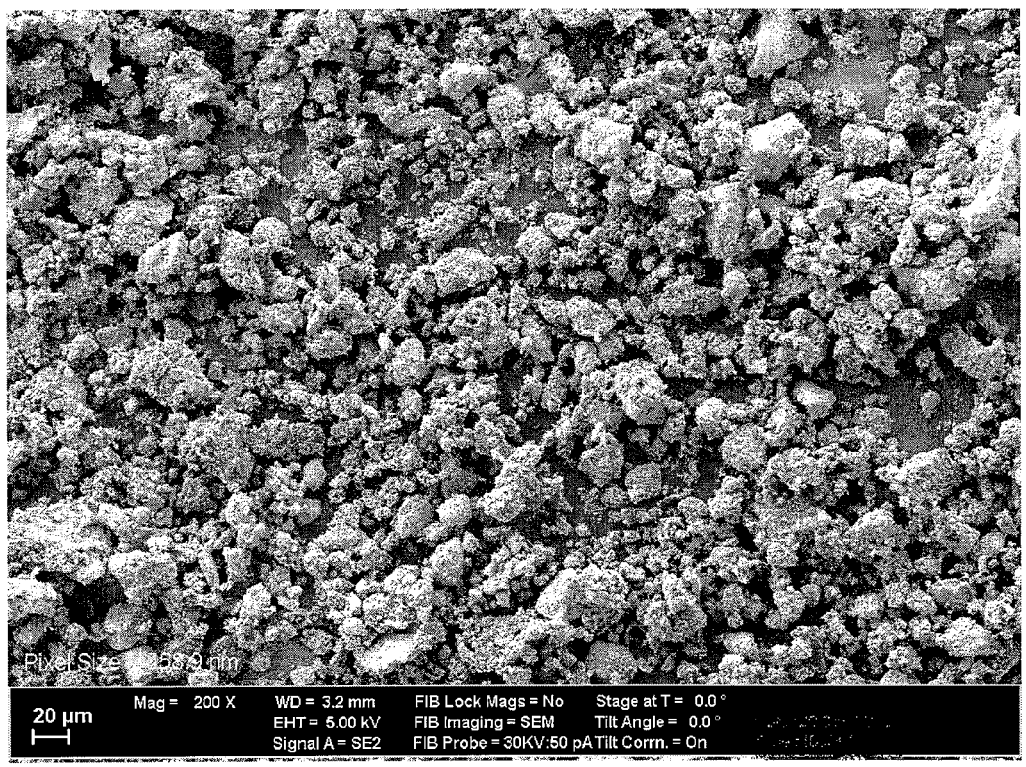
FIG. 5 shows an SEM image of a filler according to example 1 of U.S. Pat. No. 4,781,940 using OX-50 as a particulate filler.

SEM images of the materials were taken to illustrate the morphology of the particles. Scanning electron microscopy (SEM) pictures were taken using a Ultra high resolution FESEM from Zeiss. The results are shown in FIG. 5. A fluid-like movement of the particles cannot be observed.

Example 12—Filler Preparation According to the Present Invention Using OX-50

SNO-1-92-1: 40 g of treated OX-50 (treated with 5 wt.-% A-174 silane=gamma-methacryloxypropyltrimethoxysilane) were mixed with 48 g methylene chloride and 10 g of a mixture containing 61.8 wt.-% bis-GMA, 6.9 wt.-% bisphenol-A dimethacrylate, 29.4 wt.-% triethylene glycol dimethacrylate and 2.0 wt.-% radical initiator.

The mixture was homogenized by stirring and then injected into the spray dryer using its internal peristaltic pump and a 2 component jet nozzle from Büchi (nozzle diameter=1.4 mm), setting the pump rate to 20%, the rotameter to 55 mm and the inlet temperature to 75° C. The aspirator efficiency was set to 100%. Nitrogen was used as the carrier gas (drying and atomization gas).

After the agglomerated particles were spray dried, the agglomerated particles were collected and placed in a three necked round bottom flask. The flask was purged with argon gas for at least 5 minutes and tightly sealed. The flask was put in an oven at 100° C. for 3.3 hours.

Figure 6:
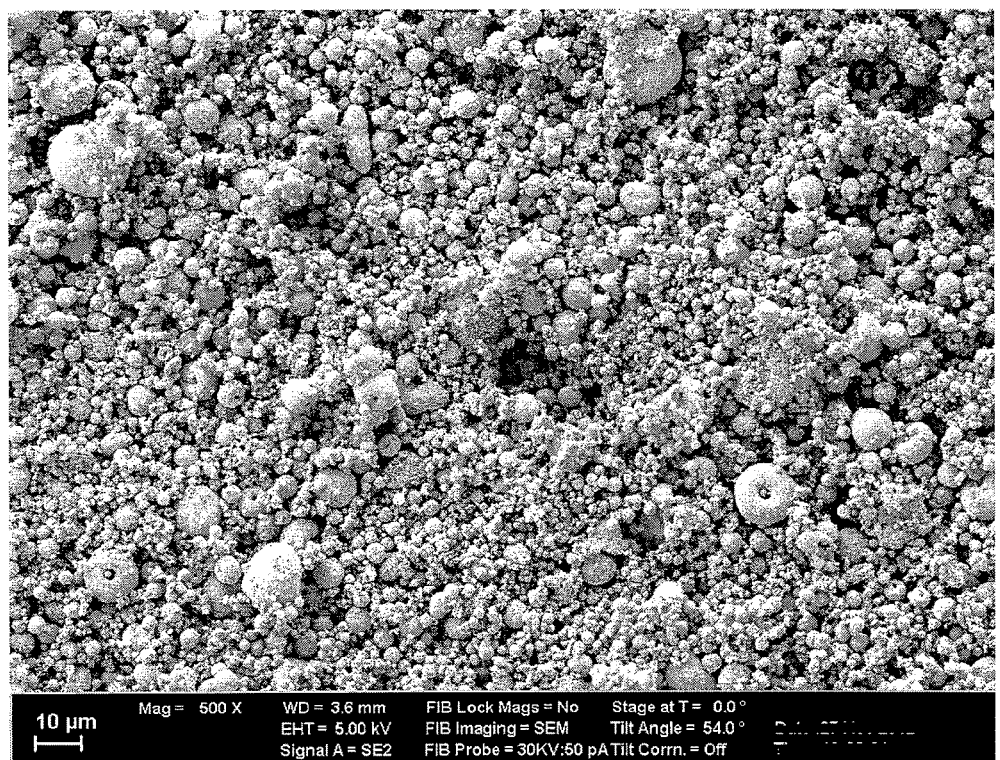
FIG. 6 show an SEM image of an agglomerated filler based on OX-50 according to the present invention

SEM images of the materials were taken to illustrate the morphology of the particles. The results are shown in FIG. 6.

Comparative Example 2—Filler Preparation According to U.S. Pat. No. 4,781,940 Using Modified Dental Glass Particles SNO-1-74-1: 150 g of a milled and silanated dental glass (strontium aluminum silicate glass—median particle size d3.50=0.6 μm were mixed with 78.6 g acetone and 22.5 g of a mixture of polymerizable methacrylate monomers (monomer mixture of the commercially available material Dyract® eXtra, comprising urethane dimethacrylate, carboxylic acid modified dimethacrylate, Triethyleneglycol dimethacrylate, Trimethacrylate resin, dimethacrlyate resin, campherquinone, ethyl-4(dimethylamino)benzoate, butylated hydroxyl toluene, UV stabilizer) and 0.26 g radical initiator.

The slurry was poured into a tray and acetone was evaporated by letting the tray stand in air at ambient temperatures (approx. 23° C.) for 16 hours. After evaporating the acetone solvent, the coated glass particles were passed through a 100 μm sieve. The sieved material was heated to 120° C. for 4 hours in a vacuum oven, or alternatively in an inert atmosphere.

Figure 7:
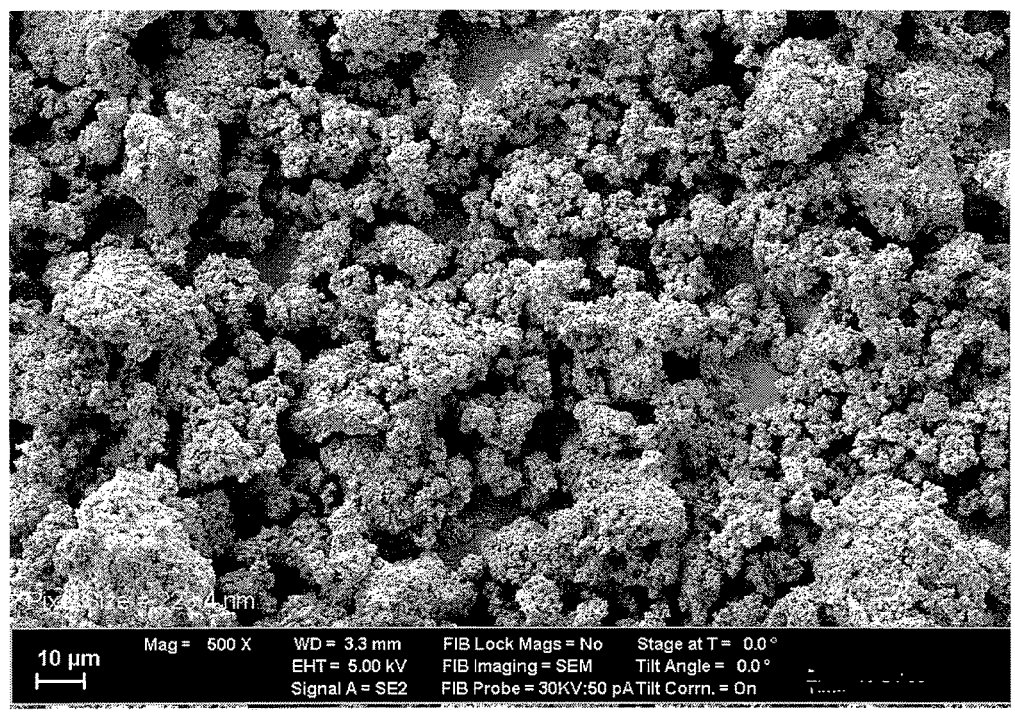
FIG. 7 shows SEM images of a filler prepared according to the method of U.S. Pat. No. 4,781,940 except that silanated dental glass as a particulate filler is used.

SEM images of the materials were taken to illustrate the morphology of the particles. The results are shown in FIG. 7. A fluid-like movement of the particles cannot be observed.

Example 13—Filler Preparation According to the Present Invention Using Modified Dental Glass Particles AZI-01-45-01: 250 g of a milled and silanated dental glass (strontium aluminum silicate glass—median particle size d3.50=0.6 µm were mixed with 140 g acetone and 37.5 g of a mixture of polymerizable methacrylate monomers (monomer mixture of the commercially available material Dyract® eXtra, comprising urethane dimethacrylate, carboxylic acid modified dimethacrylate, Triethyleneglycol dimethacrylate, Trimethacrylate resin, dimethacrlyate resin, campherquinone, ethyl-4(dimethylamino)benzoate, butylated hydroxyl toluene, UV stabilizer) and 0.43 g radical initiator.

The mixture was homogenized by stirring and then injected into the spray dryer using its internal peristaltic pump and a 2 component jet nozzle from Büchi (nozzle diameter=1.4 mm), setting the pump rate to 60%, the rotameter to 50 mm and the inlet temperature to 120° C. The aspirator efficiency was set to 100%. Nitrogen was used as the carrier gas (drying and atomization gas).

After the agglomerated particles were spray dried, the agglomerated particles were collected and placed in a three necked round bottom flask. The flask was purged with argon gas for at least 5 minutes and tightly sealed. The flask was put in an oven at 100° C. for 3.3 hours.

Figure 8:
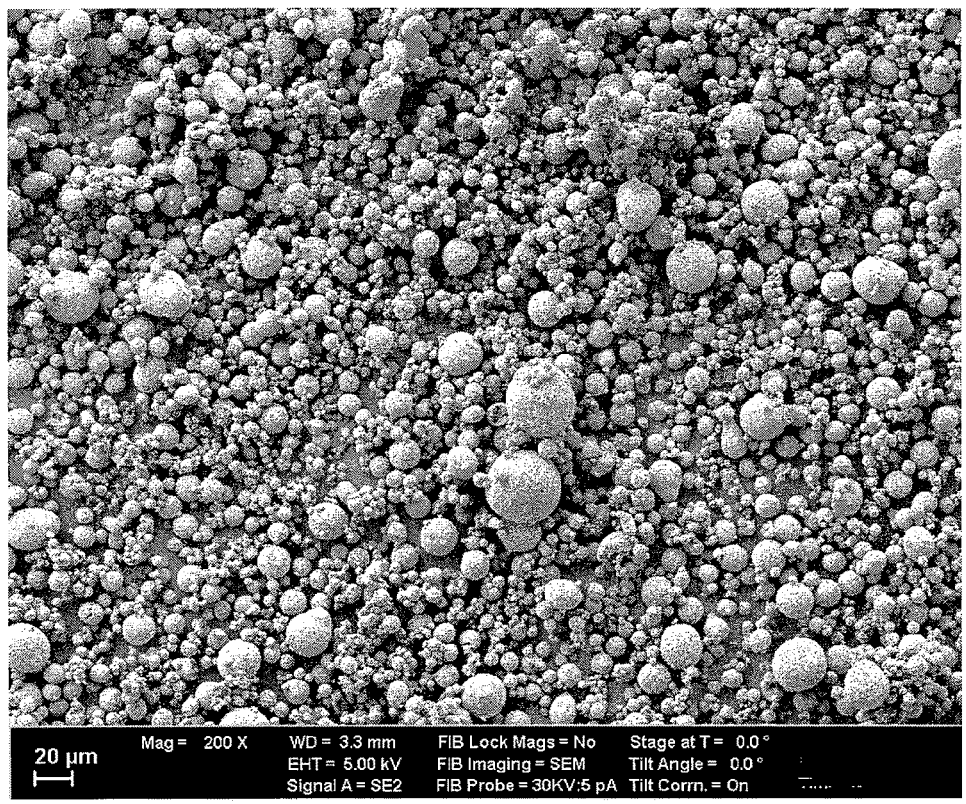
FIG. 8 shows SEM images of agglomerated fillers based on a silanated dental glass according to the present invention.

SEM images of the materials were taken to illustrate the morphology of the particles. The results are shown in FIG. 8.

Based on the SEM pictures shown in FIGS. 5 to 8, a clear difference in the morphology of the prepared agglomerated fillers can be seen. Whereas in case of U.S. Pat. No. 4,781,940 no defined shape of the agglomerated particles can be seen, the method according to the present invention clearly shows the formation of spherical particles.

The invention claimed is:

1. A process for preparation of composite filler particles, comprising the steps of:
   (a) coating a particulate glass filler having a median particle size (D50) of from 100 to 1200 nm with a coating composition containing a film-forming agent forming a coating layer on the surface of the particulate glass filler, said coating layer displaying reactive groups on the surface of the coating layer, said reactive groups being selected from addition polymerizable groups and step-growth polymerizable groups, thereby forming a coated particulate glass filler; subsequently or concurrently
   (b) agglomerating the coated particulate glass filler, for providing a granulation of the coated particulate glass filler wherein the granulation contains the coated particulate glass filler particles separated from and connected to each other by at least one coating layer, whereby the at least one coating layer may be crosslinked by crosslinking groups obtained by reacting the reactive groups of the coated layer, whereby the agglomeration is carried out by spray agglomeration;
   wherein the prepared composite filler particles have a median particle size (D50) of from 1 to 70 µm;
   wherein reactive groups are transformed into crosslinking groups by addition polymerization or step-growth polymerisation; and
   wherein the particulate glass filler is the main component by volume of the composite filler particles.

2. The process according to claim 1, wherein said reactive groups are selected from step-growth polymerizable groups.

3. The process according to claim 1, wherein the coating composition contains a film-forming agent forming a covalent bond with the particulate glass filler.

4. The process according to claim 3, wherein the covalent bond is obtained by the reaction of a hydroxyl group on the surface of the particulate glass filler and a silane group.

5. The process according to claim 1, wherein the maximum thickness of the coating layer on the particulate glass filler is less than the median particle diameter (D50) of the particulate glass filler.

6. The process according to claim 1, wherein the coating composition comprises one or more polymerizable monomers, a polymerization initiator, and a solvent.

7. The process according to claim 1, wherein the coating composition has a dynamic viscosity in the range of from 0.0001 to 15 Pas (23° C.).

8. The process according to claim 1, wherein the process is carried out in a fluidized bed.

9. The process according to claim 1, wherein the particulate glass filler particles has a median particle size (D50) in the range of from 2 µm to 20 µm.

10. The process according to claim 1, which further includes a step of treating the composite filler particles with a silanating agent or a surface active agent.

11. The process according to claim 1, wherein agglomerating the coated particulate glass filler occurs in the presence of a further crosslinking agent.

12. The process according to claim 1, wherein agglomerating the coated particulate glass filler occurs in the presence of a further particulate glass filler not displaying reactive groups.

13. The process according to claim 11, wherein the at least one coating layer is crosslinked by crosslinking groups obtained by reacting the reactive groups and the further crosslinking agent.

14. The process according to claim 1, further comprising at least one of milling, classifying or sieving the granulation of the coated particulate glass filler.

15. The process according to claim 1, further comprising crosslinking the granulation of the coated particulate glass filler.

16. The process according to claim 1, wherein the crosslinking of the at least one coating layer can occur during agglomeration or after agglomeration.

* * * * *